US009675076B2

(12) United States Patent
Li et al.

(10) Patent No.: US 9,675,076 B2
(45) Date of Patent: *Jun. 13, 2017

(54) PEROXYCARBOXYLIC ACID COMPOSITIONS SUITABLE FOR INLINE OPTICAL OR CONDUCTIVITY MONITORING

(71) Applicant: Ecolab USA Inc., St. Paul, MN (US)

(72) Inventors: Junzhong Li, Eagan, MN (US); David D. McSherry, St. Paul, MN (US); Allison Brewster, Inver Grove Heights, MN (US); Richard Staub, Lakeville, MN (US)

(73) Assignee: Ecolab USA Inc., Saint Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/413,582

(22) Filed: Jan. 24, 2017

(65) Prior Publication Data
US 2017/0127682 A1 May 11, 2017

Related U.S. Application Data

(63) Continuation of application No. 14/339,556, filed on Jul. 24, 2014, which is a continuation of application
(Continued)

(51) Int. Cl.
*A01N 59/00* (2006.01)
*A01N 37/02* (2006.01)
(Continued)

(52) U.S. Cl.
CPC ............. *A01N 59/00* (2013.01); *A01N 37/02* (2013.01); *A01N 37/16* (2013.01); *G01N 21/643* (2013.01); *G01N 2021/6439* (2013.01)

(58) Field of Classification Search
None
See application file for complete search history.

(56) References Cited

U.S. PATENT DOCUMENTS 4,587,264 A 5/1986 Jourdan-Laforte et al.
5,200,189 A 4/1993 Oakes et al.
(Continued)

FOREIGN PATENT DOCUMENTS

CA 2084172 6/1993
CA 2152908 7/1997
(Continued)

OTHER PUBLICATIONS

Database Caplus Chemical Abstracts Service, Columbus, Ohio, US; Database Accession No. 2005:492548, Abstract of JP 2005146101, Kao Corp., Japan, Hasumi et al., Jun. 9, 2005.*
(Continued)

Primary Examiner — Karl J Puttlitz
(74) Attorney, Agent, or Firm — McKee, Voorhees & Sease, PLC

(57) ABSTRACT

Peracid stable fluorescent active compounds in highly acidic, equilibrium peroxycarboxylic acid sanitizing compositions are disclosed as having improved fluorescent stability allowing for monitoring of peroxycarboxylic acid concentration by conductivity and/or optical sensors. Beneficially, the compositions are also low odor and low/no VOC dual functioning acid wash and sanitizing compositions.

7 Claims, 4 Drawing Sheets

Related U.S. Application Data

No. 13/785,405, filed on Mar. 5, 2013, now Pat. No. 8,822,719.

(51) Int. Cl.
*A01N 37/16* (2006.01)
*G01N 21/64* (2006.01)

(56) References Cited

U.S. PATENT DOCUMENTS

| | | |
|---|---|---|
| 5,314,687 A | 5/1994 | Oakes et al. |
| 5,349,083 A | 9/1994 | Brougham et al. |
| 5,415,807 A | 5/1995 | Gosselink et al. |
| 5,431,848 A | 7/1995 | Getty |
| 5,435,808 A | 7/1995 | Holzhauer et al. |
| 5,589,507 A | 12/1996 | Hall, II et al. |
| 5,624,634 A | 4/1997 | Brougham |
| 5,632,676 A | 5/1997 | Kurschner et al. |
| 5,635,195 A | 6/1997 | Hall, II et al. |
| 5,691,298 A | 11/1997 | Gosselink et al. |
| 5,718,910 A | 2/1998 | Oakes et al. |
| 5,840,343 A | 11/1998 | Hall, II et al. |
| 5,965,785 A | 10/1999 | Braden et al. |
| 5,968,893 A | 10/1999 | Manohar et al. |
| 6,004,922 A | 12/1999 | Watson et al. |
| 6,010,729 A | 1/2000 | Gutzmann et al. |
| 6,049,002 A | 4/2000 | Mattila et al. |
| 6,103,286 A | 8/2000 | Gutzmann et al. |
| 6,156,156 A | 12/2000 | Rousu et al. |
| 6,165,483 A | 12/2000 | Hei et al. |
| 6,201,110 B1 | 3/2001 | Olsen et al. |
| 6,238,685 B1 | 5/2001 | Hei et al. |
| 6,284,793 B1 | 9/2001 | Fuchs et al. |
| 6,545,047 B2 | 4/2003 | Gutzmann et al. |
| 6,627,593 B2 | 9/2003 | Hei et al. |
| 6,627,657 B1 | 9/2003 | Hilgren et al. |
| 6,635,286 B2 | 10/2003 | Hei et al. |
| 6,866,749 B2 | 3/2005 | Delmas et al. |
| 6,919,304 B2 | 7/2005 | Dykstra et al. |
| 7,060,136 B1 | 6/2006 | Zeiher et al. |
| 7,078,373 B2 | 7/2006 | Burrows et al. |
| 7,148,351 B2 | 12/2006 | Morris et al. |
| 7,169,236 B2 | 1/2007 | Zeiher et al. |
| 7,243,664 B2 | 7/2007 | Berger et al. |
| 7,448,255 B2 | 11/2008 | Hoots et al. |
| 7,601,789 B2 | 10/2009 | Morris et al. |
| 7,771,737 B2 | 8/2010 | Man et al. |
| 7,875,720 B2 | 1/2011 | Morris et al. |
| 7,887,641 B2 | 2/2011 | Man et al. |
| 7,910,371 B2 | 3/2011 | Johnson |
| 7,922,828 B2 | 4/2011 | Smith et al. |
| 7,949,432 B2 | 5/2011 | Rice |
| 7,981,679 B2 | 7/2011 | Rice |
| 7,985,318 B2 | 7/2011 | Shevchenko et al. |
| 8,017,409 B2 | 9/2011 | Tokhtuev et al. |
| 8,030,351 B2 | 10/2011 | Gutzmann et al. |
| 8,071,528 B2 | 12/2011 | Smith et al. |
| 8,084,756 B2 | 12/2011 | Tokhtuev et al. |
| 8,119,412 B2 | 2/2012 | Kraus |
| 8,178,336 B2 | 5/2012 | Derkx et al. |
| 8,236,573 B2 | 8/2012 | Tokhtuev et al. |
| 8,309,507 B2 | 11/2012 | Fernandez Prieto et al. |
| 2003/0234382 A1 | 12/2003 | Sato et al. |
| 2003/0235623 A1 | 12/2003 | Van Oosterom |
| 2004/0033269 A1 | 2/2004 | Hei et al. |
| 2004/0035537 A1 | 2/2004 | Delmas et al. |
| 2005/0281773 A1 | 12/2005 | Wieland et al. |
| 2009/0145202 A1 | 6/2009 | Tokhtuev et al. |
| 2009/0221704 A1 | 9/2009 | Aksela et al. |
| 2009/0269324 A1 | 10/2009 | Herdt et al. |
| 2010/0021557 A1 | 1/2010 | Li et al. |
| 2010/0021558 A1 | 1/2010 | Dada et al. |
| 2010/0048730 A1 | 2/2010 | Li et al. |
| 2010/0108566 A1 | 5/2010 | Scattergood et al. |
| 2010/0160449 A1 | 6/2010 | Rovison, Jr. et al. |
| 2012/0052134 A1 | 3/2012 | Li et al. |
| 2012/0085931 A1 | 4/2012 | Burns et al. |
| 2012/0149121 A1 | 6/2012 | Tokhtuev et al. |
| 2013/0018097 A1 | 1/2013 | Bolduc et al. |
| 2013/0022496 A1 | 1/2013 | Herdt et al. |
| 2014/0096971 A1 | 4/2014 | Keizer et al. |

FOREIGN PATENT DOCUMENTS

| | | |
|---|---|---|
| CN | 1751768 | 3/2006 |
| DE | 197 54 290 A1 | 6/1999 |
| DE | 19754290 | 6/1999 |
| EP | 0 061 393 | 9/1982 |
| EP | 0061393 | 9/1982 |
| EP | 0068547 | 1/1983 |
| EP | 0075419 | 3/1983 |
| EP | 0231632 | 8/1987 |
| EP | 0233730 | 8/1987 |
| EP | 0267047 | 5/1988 |
| EP | 0384911 | 8/1990 |
| EP | 0 395 902 | 11/1990 |
| EP | 0395902 | 11/1990 |
| EP | 0396341 | 11/1990 |
| EP | 0442549 | 8/1991 |
| EP | 0 280 697 | 9/1992 |
| EP | 0280697 | 9/1992 |
| EP | 0 626 371 | 11/1994 |
| EP | 0626371 | 11/1994 |
| EP | 0741776 | 11/1996 |
| EP | 0751210 | 1/1997 |
| EP | 0751933 | 8/1997 |
| EP | 0845526 | 6/1998 |
| EP | 0906950 | 4/1999 |
| EP | 1001012 | 5/2000 |
| EP | 1010749 | 6/2000 |
| EP | 1247802 | 10/2002 |
| EP | 1931628 | 6/2008 |
| EP | 2 271 410 | 10/2011 |
| EP | 2271410 | 10/2011 |
| EP | 2522714 | 11/2012 |
| EP | 2522715 | 11/2012 |
| GB | 1198734 | 7/1970 |
| GB | 1584170 | 2/1981 |
| JP | 2006-45146 | 2/2006 |
| JP | 2006-45147 | 2/2006 |
| JP | 200645146 | 2/2006 |
| JP | 200645147 | 2/2006 |
| WO | 9007501 | 7/1990 |
| WO | 9107375 | 5/1991 |
| WO | 9115474 | 10/1991 |
| WO | 9403395 | 2/1994 |
| WO | 9410284 | 5/1994 |
| WO | 9413776 | 6/1994 |
| WO | 9418299 | 8/1994 |
| WO | 9424869 | 11/1994 |
| WO | 9429509 | 12/1994 |
| WO | 9502030 | 1/1995 |
| WO | 9521122 | 8/1995 |
| WO | 9521290 | 8/1995 |
| WO | 9528471 | 10/1995 |
| WO | 9528472 | 10/1995 |
| WO | 9533816 | 12/1995 |
| WO | 9614384 | 5/1996 |
| WO | 9616148 | 5/1996 |
| WO | 9743393 | 11/1997 |
| WO | 9803513 | 1/1998 |
| WO | 9811189 | 3/1998 |
| WO | 9811777 | 3/1998 |
| WO | 9818893 | 5/1998 |
| WO | 9931215 | 6/1999 |
| WO | 9932598 | 7/1999 |
| WO | 0042145 | 7/2000 |
| WO | 0070951 | 11/2000 |
| WO | 0076963 | 12/2000 |
| WO | 0078911 | 12/2000 |
| WO | 0119414 | 3/2001 |
| WO | 0187358 | 11/2001 |
| WO | 2003006581 | 1/2003 |
| WO | 2004044266 | 5/2004 |

(56) References Cited

FOREIGN PATENT DOCUMENTS

| WO | 2008005058 | 1/2008 |
|---|---|---|
| WO | 2011089313 | 7/2011 |
| WO | 2011146557 | 11/2011 |
| WO | 2012090124 | 7/2012 |
| WO | 2012090125 | 7/2012 |

OTHER PUBLICATIONS

A.O.A.C. Germicidal and Detergent Sanitizing Action of Disinfectants, Official Methods of Analysis of the Association of Official Analytical Chemists, paragraph 960.09 and applicable sections, 15th Edition, 1990 (EPA Guideline 91-2).
A.O.A.C. Use Dilution Methods, Official Methods of Analysis of the Association of Official Analytical Chemists, paragraph 955.14 and applicable sections 15th Edition, 1990 (EPA Guidline 91.2).
Brooks, Robert E., et al., "Alkaline hydrogen peroxide bleaching of cellulose", Kluwer Academic Publishers, Cellulose 7: 263-286, 2000 (24 pages).
Carboni-Oerlemans, Chiara, et al., "Hydrolase-catalysed synthesis of peroxycarboxylic acids: Biocatalytic promiscuity for practical applications" , Elsevier, Journal of Biotechnology, 126 (2006) 140-151 (12 pages).
Chen, J., "Enhanced Alkaline Peroxide Bleaching of Softwood Kraft Pulps Using a New Activator," Journal of Pulp and Paper Science: vol. 27, No. 12, Dec. 2001 (4 pages).
Chung, L., et al., "Coordinative Binding of Divalent Cations with Ligands Related to Bacterial Spores", Biophysical Journal (1971) vol. 11, pp. 470-482.
Dannacher, Josef J., "Catalytic bleach: Most valuable applications for smart oxidation chemistry", Journal of Molecular Catalysis A: Chemical 251 (2006) 159-176.
Database Caplus Chemical Abstracts Service, Columbus, Ohio, US; Database Accession No. 1960:97225, Abstract of DE 1024514, Feb. 20, 1958, Oxidation of organic compounds with hydrogen peroxide in the liquid phase.
Effkemann, Stefan, et al., "Peroxide analysis in laundry detergents using liquid chromatography", Elsevier, Analytica Chimica Acta, 363 (1998) 97-103 (7 pages).
Junzhong Li, et al., "Stable Percarboxylic Acid Compositions and Uses Thereof", U.S. Appl. No. 13/844,515, filed Mar. 15, 2013, Applicant Ecolab USA Inc.
Katz, Jonathan, "Report: Fracking to Grow U.S. Water-Treatment Market Nine-Fold by 2020", http://www.industryweek.com/global-economy/report-fracking-grow-us-frack-water-treatment-market-nine-fold-2020, pp. 1-2, [retrieved from the internet on Jun. 6, 2012].
Lee, Jung Jin, et al., "Hydrolytic stability of a series of lactam-based cationic bleach activators and their impact on cellulose peroxide bleaching", Spring Science + Business Medica B.V., Cellulose (2010) 17:671-678 (8 pages).
Leistner (1995) In Gould GW (ed.) New Methods of Food Preservation, Springer, pp. 1-21.
Leistner, "Basic aspects of food preservation by hurdle technology", International Journal of Food Microbiology, (2000) 55: 181-186.
Leveneur, Sebastien, "Synthesis of peroxypropionic acid from propionic acid and hydrogen peroxide over heterogeneous catalysts", Elsevier, Chemical Engineering Journal, 147 (2009) 323-329 (7 pages).
Li, Junzhong, "Stable Percarboxylic Acid Compositions and Uses Thereof", filed Mar. 15, 2013, U.S. Appl. No. 13/844,515.
Maeda, Hatsuo, et al., "Assessment of Acyl Groups and Reaction Conditions in the Competition between 6 Perhydrolysis and Hydrolysis of Acyl Resorufins for Developing an Indicator Reaction for Fluorometric Analysis of Hydrogen Peroxide", Pharmaceutical Society of Japan, Cehm. Pharm. Bull. 50(2) 169-174, 2002 (6 pages).
Malow and Wehrstedt, "Prediction of the self-accelerating decomposition temperature (SADT) for liquid organic peroxides from differential scanning calorimetry (DSC) measurements", J. Hazard Mater. (2005) 120(1-3): 21-4.
Muurinene, Esa, "Organosolv Pulping—A review and distallation study related to peroxyacid pulping", Department of Process Engineering, University of Oulu, May 16, 2000, Oulu, Finland (314 pages).
Nowack, Bernd, "Environmental Chemistry of Phosphonates", Water Research (2003) vol. 37, No. 11, pp. 2533-2546.
Ogata, Y., et al., "The Formation of Peracids by the Perhydrolysis With Alkaline Hydrogen Peroxide", Tetrochem, vol. 23, pp. 3327-3332, Pergamom Press, 1967 (7 pages).
Ogata et al., "Radical scavenging activities of niacin-related compounds", Biosci. Biotechnol. Biochem., 2002, 66(3), 641-645.
Popov, Konstantin, et al., "Critical Evaluation of Stability Constants of Phosphonic Acids", Pure Appl. Chem. (2001), vol. 73, No. 10, pp. 1641-1677.
"Recommendations on the Trasnport of Dangerous Goods, Manual of Tests and Criteria", 5th revised edition (2009), UN, sect. 28.4.4, p. 314.
"Recommendations on the Trasport of Dangerous Goods, Model Regulations" (Rev. 17) ST/SG/AC. 10/1/Rev.17 (2011).
Rizkalla, E.N., et al., "Metal Chelates of Phosphonate-Containing Ligands-V Stability of some 1-Hydroxyethane-1, 1-Diphosphonic Acid Metal Chelates", Talanta (1980), vol. 27, No. 9, pp. 715-719.
Rusch gen. Klaas, Mark, et al., "Lipase-catalyzed preparation of peroxy acids and their use for expoxidation", Elsevier, Journal of Molecular Catalysis A: Chemical 117 (1997) 311-319 (9 pages).
Rusch gen. Klaas, Mark, et al., "Lipase-catalyzed conversions of trimethylsilyl ethers: deprotection, acetylation, epoxidation and one-pot-multi-step reactions", Journal of Molecular Catalysis B: Enzymatic 7 (1999) 283-289.
Rusch gen. Klaas, Mark, et al., "Biocatalylic peroxy acid formation for disinfection", Journal of Molecular Catalysis B: Enzymatic 19-20 (2002) 499-505.
Suchy, Miro, et al., "Improving Alkaline Peroxide Delignification Using a Vandium Activator", Paprican and Department of Chemistry, McGill University, Montreal, Quebec, Oct. 25-29, 1998 (15 pages).
Swern, Daniel (ed.), "Organic Peroxides", Wiley-Interscience, New York (1970), vol. 1, pp. 360-369.
Tsunokawa, Youko et al., "A Versatile Method for Preparation of 0-Alkylperoxycarbonic Acids: Epoxidation with Alkyloxycarbonylimidazoles and Hydrogen Peroxide", Tetrahedron Letters, vol. 23, No. 20, (1982), pp. 2113-2116.
Yin, De Lu (Tyler), et al., "Switching Catalysis from Hydrolysis to perhydrolysis in Pseudomonas fluorescents Esterase", Biochemistry, (2010) 49: 1931-1942.
Ecolab USA Inc., et al., PCT/IB2011/055832 filed Dec. 20, 2011, "Notification of Transmittal of the International Search Report and the Written Opinion of the International Searching Authority, or the Declaration" mailed Aug. 14, 2012, 14 pages.
Ecolab USA Inc., et al., PCT/IB2011/055830 filed Dec. 20, 2011, "Notification of Transmittal of the International Search Report and the Written Opinion of the International Searching Authority, or the Declaration" mailed Aug. 24, 2012, 8 pages.
Ecolab USA Inc., PCT/US2013/063512 filed Oct. 4, 2013, "The International Search Report and Written Opinion", mailed Dec. 26, 2013, 10 pages.
Ecolab USA Inc., PCT/US2014/017283 filed Feb. 20, 2014, "Notification of Transmittal of the Internation Search Report and the Written Opinion of the International Searching Authority, or the Declaration", mailed Apr. 28, 2014.

\* cited by examiner

PEROXYCARBOXYLIC ACID COMPOSITIONS SUITABLE FOR INLINE OPTICAL OR CONDUCTIVITY MONITORING

CROSS-REFERENCE TO RELATED APPLICATIONS

This application is a Continuation Application of U.S. Ser. No. 14/339,556 filed Jul. 24, 2014, which is a continuation of U.S. Ser. No. 13/785,405 filed Mar. 5, 2013, now U.S. Pat. No. 8,822,719, issued Sep. 2, 2014, all of which are herein incorporated by reference in their entirety.

This application is also related to U.S. Application Ser. No. 13/785,044 titled "Efficient Stabilizer in Controlling Self Accelerated Decomposition Temperature of Peroxycarboxylic Acid Compositions with Mineral Acids" and Ser. No. 13/785,047 titled "Defoamer Useful in a Peracid Composition with Anionic Surfactants," the entire contents of which are hereby expressly incorporated herein by reference.

FIELD OF THE INVENTION

The invention relates to peroxycarboxylic acid sanitizing compositions containing a peroxycarboxylic acid stable fluorescent active compound suitable for monitoring by conductivity and/or optical sensors. Beneficially, the sanitizing compositions are also low odor and low/no VOC dual functioning acid wash and sanitizing compositions, which further have favorable foam profiles and are stabilized under highly acidic conditions (e.g. high mineral acid levels) to provide improved transport and/or storage. Still further, the sanitizing compositions have improved antimicrobial efficacy in comparison to conventional mixed peroxycarboxylic acid compositions for sanitizing applications, while providing the various additional benefits according to the invention.

BACKGROUND OF THE INVENTION

Peroxycarboxylic acids (i.e. peracids) are commercially-available antimicrobials, sanitizing agents and/or bleaching agents, which are generally sold in equilibrium solutions containing the corresponding carboxylic acid to the peroxycarboxylic acid, hydrogen peroxide and water. Antimicrobial compositions are used in a variety of automated processing and cleaning applications to reduce microbial or viral populations on hard or soft surfaces or in a body or stream of water. For example, antimicrobial compositions are used in various applications including kitchens, bathrooms, factories, hospitals and dental offices. Antimicrobial compositions are also useful in the cleaning or sanitizing of containers, processing facilities or equipment in the food service or food processing industries, such as cold or hot aseptic packaging. Antimicrobial compositions are also used in many other applications including but not limited to clean-in-place systems (CIP), clean-out-of-place systems (COP), washer-decontaminators, sterilizers, textile laundry machines, filtration systems, etc.

Regardless of the application, an antimicrobial or "use" composition is a composition containing a defined minimum concentration of one or more active components which exhibit desired antimicrobial properties. The concentration of active components in the use composition is chosen to achieve the requisite level of antimicrobial activity. In use compositions in which one or more peracids are the active component, the concentration of hydrogen peroxide tends to increase over time while the concentration of peracid decreases. However, in order to maintain the requisite level of antimicrobial activity, the amount of peracid in the use composition must be maintained at a defined minimum concentration. In addition, as the amount of hydrogen peroxide in the use composition increases, the use composition may exceed a defined maximum concentration of hydrogen peroxide in the solution.

To ensure the amount of peracid is maintained at or above some minimum concentration and to determine when the amount of hydrogen peroxide reaches or exceeds a maximum concentration, it is necessary to determine the concentration of peracid(s) and hydrogen peroxide in the use composition. In the past, to determine both the peracid concentration and the hydrogen peroxide concentration in a use composition has required multiple time consuming manual titrations, several different reagents and relatively large volumes of use composition. Moreover, past devices and methods for determining both peracid and hydrogen peroxide concentrations were effective over only a narrow range of concentrations.

Accordingly, it is an objective of the claimed invention to develop peracid compositions having various beneficial aspects, including compatibility for monitoring of peracid concentration by conductivity and/or optical sensors.

A further object of the invention is to provide a highly acidic, mixed peroxycarboxylic acid composition having such compatibility for concentration monitoring that is also low/no VOC, low odor, low foaming and stabilized under such highly acidic conditions (e.g. mineral acids in formulation).

Other objects, advantages and features of the present invention will become apparent from the following specification taken in conjunction with the accompanying drawings.

BRIEF SUMMARY OF THE INVENTION

The present invention relates to peroxycarboxylic acid compositions which are traceable by monitoring the peracid concentration by conductivity and/or optical sensors, and uses thereof. An advantage of the invention is that the unconventionally acidic peroxycarboxylic acid compositions, including mixed peroxycarboxylic acids with mineral acids, are combined with at least one fluorescent active compound for long-term stability of the traceable component of the peroxycarboxylic acid composition concentrations. However, the fluorescent active compounds are also stable in alkaline environments providing traceable and/or measurable components. As a result, the compositions can be monitored by optical sensors and provided for broad applications of use, without impacting antimicrobial and/or sanitizing efficacy of the compositions. It is an advantage of the present invention that the peroxycarboxylic acid compositions provide other benefits including effective stabilization of the compositions presenting reduced storage and/or transportation hazards, as well as providing low foaming characteristics.

In an embodiment, the present invention is directed to an equilibrium peracid composition comprising: a $C_1$-$C_{22}$ peroxycarboxylic acid; a $C_1$-$C_{22}$ carboxylic acid; hydrogen peroxide; and a fluorescent active compound. In a further aspect, the fluorescent active compound is stable in the equilibrium peracid composition for monitoring peroxycarboxylic acid concentration by optical sensors. In a further aspect, the composition comprises from about 1 wt-% to about 40 wt-% of the $C_1$-$C_{22}$ peroxycarboxylic acid, from about 1 wt-% to about 80 wt-% of the $C_1$-$C_{22}$ carboxylic acid, from about 1 wt-% to about 80 wt-% of the hydrogen peroxide, and from about 0.001 wt-% to about 10 wt-% of the fluorescent active compound.

In an embodiment, the present invention is directed to methods for monitoring a concentration of peroxycarboxylic acid and/or hydrogen peroxide in a sanitizing composition and/or cleaning process includes providing an equilibrium peroxycarboxylic acid composition comprising a $C_1$-$C_{22}$ peroxycarboxylic acid, a $C_1$-$C_{22}$ carboxylic acid, hydrogen peroxide, and a fluorescent active compound, and wherein the fluorescent active compound is stable in the equilibrium peracid composition for monitoring peroxycarboxylic acid concentration, including for example by optical sensors. The method further includes measuring a fluorescence response with a fluorometer from the fluorescent active compound in the peroxycarboxylic acid composition or measuring an optical response from the fluorescent active compound in an optical cell, and determining a concentration of the peroxycarboxylic acid and/or the hydrogen peroxide.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
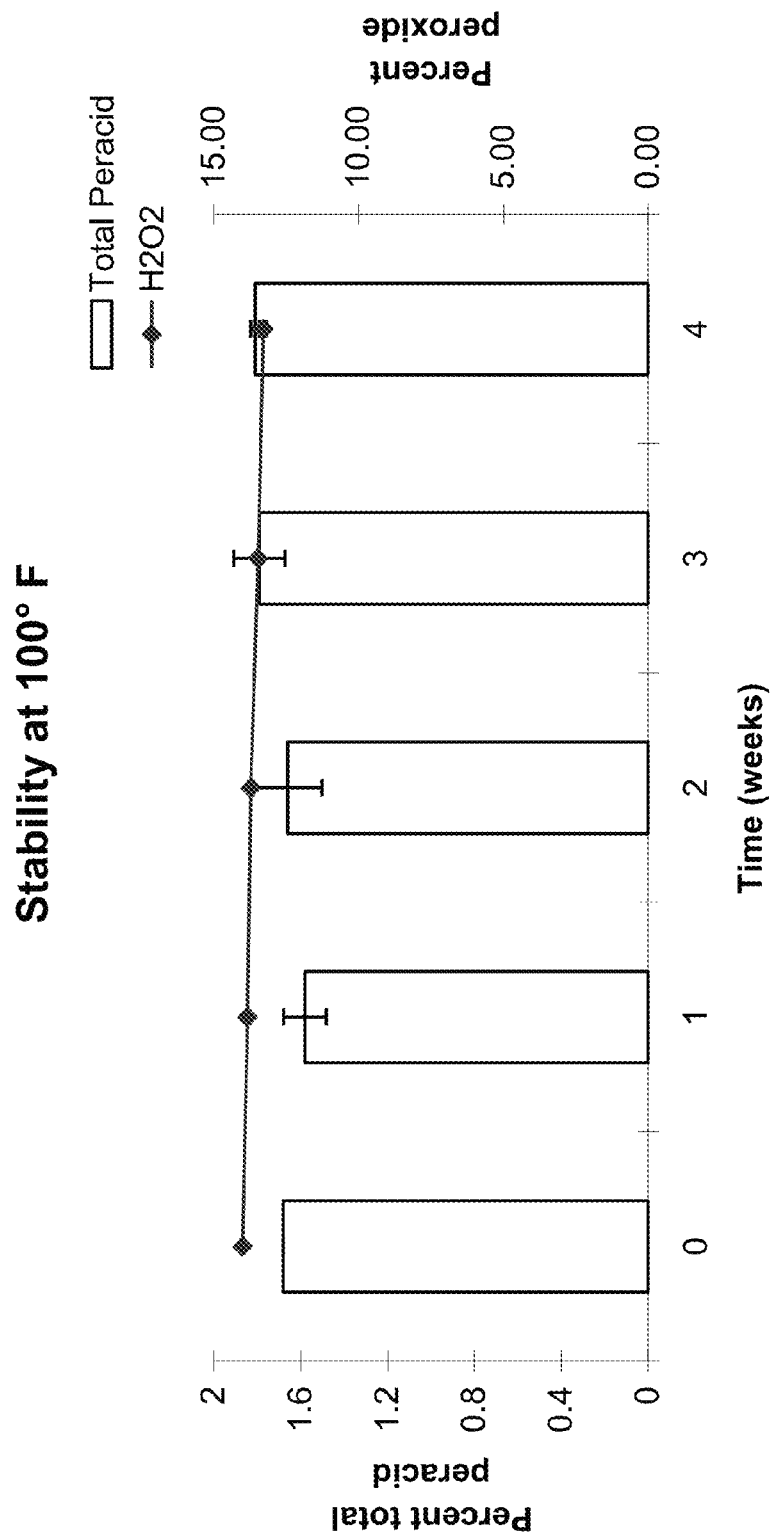
FIG. 1 shows a graph of the traceability of the peroxycarboxylic acid concentration of the highly acidic peroxycarboxylic acid compositions according to embodiments of the invention.

Various embodiments of the present invention will be described in detail with reference to the drawings, wherein like reference numerals represent like parts throughout the several views. Reference to various embodiments does not limit the scope of the invention. Figures represented herein are not limitations to the various embodiments according to the invention and are presented for exemplary illustration of the invention.

DETAILED DESCRIPTION OF THE PREFERRED EMBODIMENT

The embodiments of this invention are not limited to particular traceable highly acidic peroxycarboxylic acid compositions and methods of using the same, which can vary and are understood by skilled artisans. It is further to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form.

Numeric ranges recited within the specification are inclusive of the numbers defining the range and include each integer within the defined range. Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

The term "about," as used herein, refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

As used herein, the term "cleaning" refers to a method used to facilitate or aid in soil removal, bleaching, microbial population reduction, and any combination thereof. As used herein, the term "microorganism" refers to any noncellular or unicellular (including colonial) organism. Microorganisms include all prokaryotes. Microorganisms include bacteria (including cyanobacteria), spores, lichens, fungi, protozoa, virinos, viroids, viruses, phages, and some algae. As used herein, the term "microbe" is synonymous with microorganism.

As used herein, the term "disinfectant" refers to an agent that kills all vegetative cells including most recognized pathogenic microorganisms, using the procedure described in *A.O.A.C. Use Dilution Methods*, Official Methods of Analysis of the Association of Official Analytical Chemists, paragraph 955.14 and applicable sections, 15th Edition, 1990 (EPA Guideline 91-2). As used herein, the term "high level disinfection" or "high level disinfectant" refers to a compound or composition that kills substantially all organisms, except high levels of bacterial spores, and is effected with a chemical germicide cleared for marketing as a sterilant by the Food and Drug Administration. As used herein, the term "intermediate-level disinfection" or "intermediate level disinfectant" refers to a compound or composition that kills mycobacteria, most viruses, and bacteria with a chemical germicide registered as a tuberculocide by the Environmental Protection Agency (EPA). As used herein, the term "low-level disinfection" or "low level disinfectant" refers to a compound or composition that kills some viruses and bacteria with a chemical germicide registered as a hospital disinfectant by the EPA.

The term "hard surface" refers to a solid, substantially non-flexible surface such as a counter top, tile, floor, wall, panel, window, plumbing fixture, kitchen and bathroom furniture, appliance, engine, circuit board, and dish. Hard surfaces may include for example, health care surfaces and food/plant/animal processing surfaces.

As used herein, the terms "mixed" or "mixture" when used relating to "percarboxylic acid composition," "percarboxylic acids," "peroxycarboxylic acid composition" or "peroxycarboxylic acids" refer to a composition or mixture including more than one percarboxylic acid or peroxycarboxylic acid.

For the purpose of this patent application, successful microbial reduction is achieved when the microbial populations are reduced by at least about 50%, or by significantly more than is achieved by a wash with water. Larger reductions in microbial population provide greater levels of protection. Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can affect two kinds of microbial cell damage. The first is a lethal, irreversible action resulting in complete microbial cell destruction or incapacitation. The second type of cell damage is reversible, such that if the organism is rendered free of the agent, it can again multiply. The former is termed microbiocidal and the later, microbistatic. A sanitizer and a disinfectant are, by definition, agents which provide antimicrobial or microbiocidal activity. In contrast, a preservative is generally described as an inhibitor or microbistatic composition As used herein, the term "sanitizer" refers to an agent that reduces the number of bacterial contaminants to safe levels as judged by public health requirements. In an embodiment, sanitizers for use in this invention will provide at least a 99.999% reduction (5-log order reduction). These reductions can be evaluated using a procedure set out in *Germicidal and Detergent Sanitizing Action of Disinfectants*, Official Methods of Analysis of the Association of Official Analytical Chemists, paragraph 960.09 and applicable sections, 15th Edition, 1990 (EPA Guideline 91-2). According to this reference a sanitizer should provide a 99.999% reduction (5-log order reduction) within 30 seconds at room temperature, 25±2° C., against several test organisms.

As used herein, the term "sulfoperoxycarboxylic acid," "sulfonated peracid," or "sulfonated peroxycarboxylic acid" refers to the peroxycarboxylic acid form of a sulfonated carboxylic acid. In some embodiments, the sulfonated peracids of the present invention are mid-chain sulfonated peracids. As used herein, the term "mid-chain sulfonated peracid" refers to a peracid compound that includes a sulfonate group attached to a carbon that is at least one carbon (e.g., the three position or further) from the carbon of the percarboxylic acid group in the carbon backbone of the percarboxylic acid chain, wherein the at least one carbon is not in the terminal position. As used herein, the term "terminal position," refers to the carbon on the carbon backbone chain of a percarboxylic acid that is furthest from the percarboxyl group.

The term "weight percent," "wt-%," "percent by weight," "% by weight," and variations thereof, as used herein, refer to the concentration of a substance as the weight of that substance divided by the total weight of the composition and multiplied by 100. It is understood that, as used here, "percent," "%," and the like are intended to be synonymous with "weight percent," "wt-%," etc.

The methods and compositions of the present invention may comprise, consist essentially of, or consist of the components and ingredients of the present invention as well as other ingredients described herein. As used herein, "consisting essentially of" means that the methods and compositions may include additional steps, components or ingredients, but only if the additional steps, components or ingredients do not materially alter the basic and novel characteristics of the claimed methods and compositions.

Compositions

While an understanding of the mechanism is not necessary to practice the present invention and while the present invention is not limited to any particular mechanism of action, it is contemplated that, in some embodiments, equilibrium peroxycarboxylic acid compositions are formulated to preferably provide highly acidic compositions with a stable fluorescent active compound allowing for dose quantification, e.g. optical measurement. The formulation of stable fluorescent active compounds into highly acidic equilibrium peroxycarboxylic acid compositions allows quantification over extended periods of time; e.g. beyond the 48 hours of prior art peracid compositions that are combined with a fluorescent component at a point of use. Beneficially, this allows formulation of the peroxycarboxylic acid compositions to include the fluorescent active compound instead of such point of use dosing with a fluorescent compound as previously done in some applications of use. In addition, the present invention is a significant improvement over peroxycarboxylic acid-forming and/or containing compositions which merely contain a non-stable fluorescent compound that is only suitable for visual assessment of peracid under UV light and in dry conditions to confirm a disinfectant was applied. As a result, the concentrated equilibrium compositions containing the stable fluorescent active compounds are suitable for optical measurement of peracid concentrations in various applications of use, including for example, clean-in-place, warewashing and other sanitizing applications, rather than merely a visual assessment of a treated surface.

In an aspect, the compositions include concentrated equilibrium compositions comprising peracid(s), hydrogen peroxide, carboxylic acid(s), a solvent, e.g., water, a fluorescent active compound, and other optional additional functional ingredients (e.g. stabilizing agent, a surfactant and/or defoaming agent). In an aspect, the compositions include the exemplary ranges shown in Table 1 in weight percentage of the liquid concentrated equilibrium compositions.

TABLE 1

| Material | First Exemplary Range wt-% | Second Exemplary Range wt-% | Third Exemplary Range wt-% |
| --- | --- | --- | --- |
| Solvent (e.g. Water) | 1-75 | 10-60 | 20-40 |
| Peroxycarboxylic Acid | 0.1-40 | 1-40 | 1-20 |
| Carboxylic Acid | 0.1-90 | 1-80 | 1-50 |
| Hydrogen Peroxide | 1-90 | 1-80 | 1-50 |
| Mineral Acid | 0-50 | 0-20 | 0.1-20 |
| Fluorescent Active Compound | 0.001-10 | 0.1-10 | 0.5-7.5 |

TABLE 1-continued

| Material | First Exemplary Range wt-% | Second Exemplary Range wt-% | Third Exemplary Range wt-% |
|---|---|---|---|
| Surfactant | 0-40 | 0.1-25 | 1-20 |
| Additional Functional Ingredients (e.g. stabilizing agent, defoaming agent) | 0-25 | 0-20 | 0-10 |

In yet other aspects, the compositions according to the invention may include non-equilibrium peracid compositions, such as where a peroxycarboxylic acid is generated in situ and/or on site through a process by one or more composition (e.g. one or more part systems) comprising individual reagents combined according to the invention. In an exemplary aspect, these reagents are described herein individually along and include at least one ester of a polyhydric alcohol and a C1 to C18 carboxylic acid, an oxidizing agent, a source of alkalinity, solvents, and other functional groups/agents. An acidulant is also described herein as a reagent to be added to the compositions after the formation of the percarboxylic acid(s). Alternatively, as described herein, there may be benefits to providing the reagents in various premix formulations to decrease the number of reagents and/or increase the simplicity of the invention for generating peracid compositions for a particular use. Premix formulations suitable for use according to the invention may comprise, consist of and/or consist essentially of at least one ester of a polyhydric alcohol and a C1 to C18 carboxylic acid, an oxidizing agent, a solvent and mixtures thereof. Premix formulations suitable for use according to the invention may also comprise, consist of and/or consist essentially of at least one ester, an oxidizing agent, water, solvents, dispersing agents, surfactants, defoamers and mixtures thereof.

In some aspects the compositions, whether generated in situ or on site from one or more premix compositions or whether provided in a concentrated equilibrium composition, in a use solution have either an alkaline and/or acid pH. However, in some aspects, the concentrated equilibrium compositions in a use solution have a pH at about 4 or less. Preferably, the compositions in a use solution have a pH at about 3 or less. In an aspect, the use solutions of the highly acidic, stabilized peroxycarboxylic acid compositions, when diluted pursuant to EPA sanitizer suspension preparations (e.g. dilute 1 oz. of the peracid composition to 8 Gallon with 500 ppm hard water), such that the pH of the solution is less than about 3.0, preferably between about 2.8-2.9.

Peracids

According to the invention, a peroxycarboxylic acid (i.e. peracid) is included for antimicrobial efficacy in the sanitizing compositions disclosed herein. As used herein, the term "peracid" may also be referred to as a "percarboxylic acid," "peroxycarboxylic acid" or "peroxyacid." Sulfoperoxycarboxylic acids, sulfonated peracids and sulfonated peroxycarboxylic acids are also included within the terms "peroxycarboxylic acid" and "peracid" as used herein. The terms "sulfoperoxycarboxylic acid," "sulfonated peracid," or "sulfonated peroxycarboxylic acid" refers to the peroxycarboxylic acid form of a sulfonated carboxylic acid as disclosed in U.S. Pat. No. 8,344,026, and U.S. Patent Publication Nos. 2010/0048730 and 2012/0052134, each of which are incorporated herein by reference in their entirety. As one of skill in the art appreciates, a peracid refers to an acid having the hydrogen of the hydroxyl group in carboxylic acid replaced by a hydroxy group. Oxidizing peracids may also be referred to herein as peroxycarboxylic acids.

A peracid includes any compound of the formula R—(COOOH)$_n$, in which R can be hydrogen, alkyl, alkenyl, alkyne, acylic, alicyclic group, aryl, heteroaryl, or heterocyclic group, and n is 1, 2, or 3, and named by prefixing the parent acid with peroxy. Preferably R includes hydrogen, alkyl, or alkenyl. The terms "alkyl," "alkenyl," "alkyne," "acylic," "alicyclic group," "aryl," "heteroaryl," and "heterocyclic group" are as defined herein.

As used herein, the term "alkyl" or "alkyl groups" refers to saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups). Preferably, a straight or branched saturated aliphatic hydrocarbon chain having from 1 to 22 carbon atoms, such as, for example, methyl, ethyl, propyl, isopropyl (1-methylethyl), butyl, tert-butyl (1,1-dimethylethyl), and the like.

Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including heteroaromatic) groups.

The term "alkenyl" includes an unsaturated aliphatic hydrocarbon chain having from 2 to 12 carbon atoms, such as, for example, ethenyl, 1-propenyl, 2-propenyl, 1-butenyl, 2-methyl-1-propenyl, and the like. The alkyl or alkenyl can be terminally substituted with a heteroatom, such as, for example, a nitrogen, sulfur, or oxygen atom, forming an aminoalkyl, oxyalkyl, or thioalkyl, for example, aminomethyl, thioethyl, oxypropyl, and the like. Similarly, the above alkyl or alkenyl can be interrupted in the chain by a heteroatom forming an alkylaminoalkyl, alkylthioalkyl, or alkoxyalkyl, for example, methylaminoethyl, ethylthiopropyl, methoxymethyl, and the like.

Further, as used herein the term "alicyclic" includes any cyclic hydrocarbyl containing from 3 to 8 carbon atoms. Examples of suitable alicyclic groups include cyclopropanyl, cyclobutanyl, cyclopentanyl, etc. In some embodiments, substituted alkyls can include a heterocyclic group. As used herein, the term "heterocyclic group" includes closed ring structures analogous to carbocyclic groups in which one or more of the carbon atoms in the ring is an element other than carbon, for example, nitrogen, sulfur or oxygen. Heterocyclic groups may be saturated or unsaturated. Exemplary heterocyclic groups include, but are not limited to, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan. Additional examples of suitable heterocyclic groups include groups derived from tetrahydrofurans, furans, thiophenes, pyrrolidines, piperidines, pyridines, pyrrols, picoline, coumaline, etc.

According to the invention, alkyl, alkenyl, alicyclic groups, and heterocyclic groups can be unsubstituted or substituted by, for example, aryl, heteroaryl, $C_{1-4}$ alkyl, $C_{1-4}$ alkenyl, $C_{1-4}$ alkoxy, amino, carboxy, halo, nitro, cyano, —$SO_3H$, phosphono, or hydroxy. When alkyl, alkenyl, alicyclic group, or heterocyclic group is substituted, preferably the substitution is $C_{1-4}$ alkyl, halo, nitro, amido, hydroxy, carboxy, sulpho, or phosphono. In one embodiment, R includes alkyl substituted with hydroxy. The term "aryl" includes aromatic hydrocarbyl, including fused aromatic rings, such as, for example, phenyl and naphthyl. The term "heteroaryl" includes heterocyclic aromatic derivatives having at least one heteroatom such as, for example, nitrogen, oxygen, phosphorus, or sulfur, and includes, for example, furyl, pyrrolyl, thienyl, oxazolyl, pyridyl, imidazolyl, thiazolyl, isoxazolyl, pyrazolyl, isothiazolyl, etc. The term "heteroaryl" also includes fused rings in which at least one ring is aromatic, such as, for example, indolyl, purinyl, benzofuryl, etc.

According to the invention, aryl and heteroaryl groups can be unsubstituted or substituted on the ring by, for example, aryl, heteroaryl, alkyl, alkenyl, alkoxy, amino, carboxy, halo, nitro, cyano, —$SO_3H$, phosphono, or hydroxy. When aryl, aralkyl, or heteroaryl is substituted, preferably the substitution is $C_{1-4}$ alkyl, halo, nitro, amido, hydroxy, carboxy, sulpho, or phosphono. In one embodiment, R includes aryl substituted with $C_{1-4}$ alkyl.

Peracids suitable for use include any peroxycarboxylic acids, including varying lengths of peroxycarboxylic acids (e.g. C1-22) that can be prepared from the acid-catalyzed equilibrium reaction between a carboxylic acid described above and hydrogen peroxide. A peroxycarboxylic acid can also be prepared by the auto-oxidation of aldehydes or by the reaction of hydrogen peroxide with an acid chloride, acid hydride, carboxylic acid anhydride, sodium alcoholate or alkyl and aryl esters. Alternatively, peracids can be prepared through non-equilibrium reactions, which may be generated for use in situ, such as the methods disclosed in U.S. Patent Publication Nos. 2012/0172440 and 2012/0172441 each titled "In Situ Generation of Peroxycarboxylic Acids at Alkaline pH, and Methods of Use Thereof," which are incorporated herein by reference in their entirety. Preferably a composition of the invention includes peroxyacetic acid, peroxyoctanoic acid, peroxypropionic acid, peroxylactic acid, peroxyheptanoic acid, peroxyoctanoic acid and/or peroxynonanoic acid.

In some embodiments, a peroxycarboxylic acid includes at least one water-soluble peroxycarboxylic acid in which R includes alkyl of 1-22 carbon atoms. For example, in one embodiment, a peroxycarboxylic acid includes peroxyacetic acid. In another embodiment, a peroxycarboxylic acid has R that is an alkyl of 1-22 carbon atoms substituted with a hydroxyl group or other polar substituent such that the substituent improves the water solubility. Methods of preparing peroxyacetic acid are known to those of skill in the art including those disclosed in U.S. Pat. No. 2,833,813, which is herein incorporated herein by reference in its entirety.

In another embodiment, a sulfoperoxycarboxylic acid has the following formula:

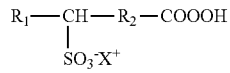

wherein $R_1$ is hydrogen, or a substituted or unsubstituted alkyl group; $R_2$ is a substituted or unsubstituted alkylene group; X is hydrogen, a cationic group, or an ester forming moiety; or salts or esters thereof. In some embodiments, $R_1$ is a substituted or unsubstituted Cm alkyl group; X is hydrogen a cationic group, or an ester forming moiety; $R_2$ is a substituted or unsubstituted $C_n$ alkyl group; m=1 to 10; n=1 to 10; and m+n is less than 18, or salts, esters or mixtures thereof.

In some embodiments, $R_1$ is hydrogen. In other embodiments, $R_1$ is a substituted or unsubstituted alkyl group. In some embodiments, $R_1$ is a substituted or unsubstituted alkyl group that does not include a cyclic alkyl group. In some embodiments, $R_1$ is a substituted alkyl group. In some embodiments, $R_1$ is an unsubstituted $C_1$-$C_9$ alkyl group. In some embodiments, $R_1$ is an unsubstituted $C_7$ or $C_8$ alkyl. In other embodiments, $R_1$ is a substituted $C_8$-$C_{10}$ alkylene group. In some embodiments, $R_1$ is a substituted $C_8$-$C_{10}$ alkyl group is substituted with at least 1, or at least 2 hydroxyl groups. In still yet other embodiments, $R_1$ is a substituted $C_1$-$C_9$ alkyl group. In some embodiments, $R_1$ is a substituted $C_1$-$C_9$ substituted alkyl group is substituted with at least 1 $SO_3H$ group. In other embodiments, $R_1$ is a $C_9$-$C_{10}$ substituted alkyl group. In some embodiments, $R_1$ is a substituted $C_9$-$C_{10}$ alkyl group wherein at least two of the carbons on the carbon backbone form a heterocyclic group. In some embodiments, the heterocyclic group is an epoxide group.

In some embodiments, $R_2$ is a substituted $C_1$-$C_{10}$ alkylene group. In some embodiments, $R_2$ is a substituted $C_8$-$C_{10}$ alkylene. In some embodiments, $R_2$ is an unsubstituted $C_6$-$C_9$ alkylene. In other embodiments, $R_2$ is a $C_8$-$C_{10}$ alkylene group substituted with at least one hydroxyl group. In some embodiments, $R_2$ is a $C_{10}$ alkylene group substituted with at least two hydroxyl groups. In other embodiments, $R_2$ is a $C_8$ alkylene group substituted with at least one $SO_3H$ group. In some embodiments, $R_2$ is a substituted $C_9$ group, wherein at least two of the carbons on the carbon backbone form a heterocyclic group. In some embodiments, the heterocyclic group is an epoxide group. In some embodiments, $R_1$ is a $C_8$-$C_9$ substituted or unsubstituted alkyl, and $R_2$ is a $C_7$-$C_8$ substituted or unsubstituted alkylene.

These and other suitable sulfoperoxycarboxylic acid compounds for use in the stabilized peroxycarboxylic acid compositions of the invention are further disclosed in U.S. Pat. No. 8,344,026 and U.S. Patent Publication Nos. 2010/0048730 and 2012/0052134, which are incorporated herein by reference in its entirety.

In additional embodiments a sulfoperoxycarboxylic acid is combined with a single or mixed peroxycarboxylic acid composition, such as a sulfoperoxycarboxylic acid with peroxyacetic acid and peroxyoctanoic acid. (PSOA/POOA/POAA). In other embodiments, a mixed peracid is employed, such as a peroxycarboxylic acid including at least one peroxycarboxylic acid of limited water solubility in which R includes alkyl of 5-22 carbon atoms and at least one water-soluble peroxycarboxylic acid in which R includes alkyl of 1-4 carbon atoms. For example, in one embodiment, a peroxycarboxylic acid includes peroxyacetic acid and at least one other peroxycarboxylic acid such as those named above. Preferably a composition of the invention includes peroxyacetic acid and peroxyoctanoic acid, such as disclosed in U.S. Pat. No. 5,314,687 which is herein incorporated by reference in its entirety. In an aspect, the peracid mixture is a hydrophilic peracetic acid and a hydrophobic peroctanoic acid, providing antimicrobial synergy. In an aspect, the synergy of a mixed peracid system allows the use of lower dosages of the peracids.

In another embodiment, a tertiary peracid mixture composition, such as peroxysulfonated oleic acid, peracetic acid and peroctanoic acid are employed, such as disclosed in U.S. Pat. No. 8,344,026 which is incorporated herein by reference in its entirety. Advantageously, a combination of peroxycarboxylic acids provides a composition with desirable antimicrobial activity in the presence of high organic soil loads. The mixed peroxycarboxylic acid compositions often provide synergistic micro efficacy. Accordingly, compositions of the invention can include a peroxycarboxylic acid, or mixtures thereof.

Various commercial formulations of peracids are available, including for example peracetic acid (approximately 15%) available as EnviroSan (Ecolab, Inc., St. Paul Minn.). Most commercial peracid solutions state a specific percarboxylic acid concentration without reference to the other chemical components in a use solution. However, it should be understood that commercial products, such as peracetic acid, will also contain the corresponding carboxylic acid (e.g. acetic acid), hydrogen peroxide and water.

In an aspect, any suitable $C_1$-$C_{22}$ percarboxylic acid can be used in the present compositions. In some embodiments, the $C_1$-$C_{22}$ percarboxylic acid is a $C_2$-$C_{20}$ percarboxylic acid. In other embodiments, the $C_1$-$C_{22}$ percarboxylic is a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$ carboxylic acid. In still other embodiments, the $C_1$-$C_{22}$ percarboxylic acid comprises peroxyacetic acid, peroxyoctanoic acid and/or peroxysulfonated oleic acid.

In an aspect of the invention, a peracid may be selected from a concentrated composition having a ratio of hydrogen peroxide to peracid from about 0:10 to about 10:0, preferably from about 0.5:10 to about 10:0.5, preferably from about 1:8 to 8:1. Various concentrated peracid compositions having the hydrogen peroxide to peracid ratios of about 0.5:10 to about 10:0.5, preferably from about 1:8 to 8:1, may be employed to produce a use solution for treatment according to the methods of the invention. In a further aspect of the invention, a peracid may have a ratio of hydrogen peroxide to peracid as low as from about 0.01 part hydrogen peroxide to about 1 part peracid. Without limiting the scope of invention, the numeric ranges are inclusive of the numbers defining the range and include each integer within the defined range.

Obtaining the preferred hydrogen peroxide to peroxycarboxylic acid ratios in a peracid composition may be obtained by a variety of methods suitable for producing a very low hydrogen peroxide to peracid ratio. In an aspect, equilibrium peracid compositions may be distilled to recover a very low hydrogen peroxide peracid mixture. In yet another aspect, catalysts for hydrogen peroxide decomposition may be combined with a peracid composition, including for example, peroxide-reducing agents and/or other biomimetic complexes. In yet another aspect, perhydrolysis of peracid precursors, such as esters (e.g. triacetin) and amides may be employed to obtain peracids with very low hydrogen peroxide. These and other methods of reducing hydrogen peroxide ratios in a peracid composition are disclosed in U.S. Patent Publication Nos. US2013/0259743A1 (Ecolab 3031USU1) titled "Use of Peracetic Acid/Hydrogen Peroxide and Catalase for Treatment of Drilling Fluids, Frac Fluids, Flowback Water and Disposal Water, and US2013/0264293A1 and US2013/0264059A1 (3031USI1 and 3031USI2) both titled "Use of Peracetic Acid/Hydrogen Peroxide and Peroxide Reducing Agents for Treatment of Drilling Fluids, Frac Fluids, Flowback Water and Disposal Water," each of which are herein incorporated by reference in their entirety.

In a preferred aspect, the $C_1$-$C_{22}$ percarboxylic acid can be used at any suitable concentration. In some embodiments, the $C_1$-$C_{22}$ percarboxylic acid has a concentration from about 0.1 wt-% to about 40 wt-% in a concentrated equilibrium composition. In other embodiments, the $C_1$-$C_{22}$ percarboxylic acid has a concentration from about 1 wt-% to about 40 wt-%, or from about 1 wt-% to about 20 wt-%. In still other embodiments, the $C_1$-$C_{22}$ percarboxylic acid has a concentration at about 1 wt-%, 2 wt-%, 3 wt-%, 4 wt-%, 5 wt-%, 6 wt-%, 7 wt-%, 8 wt-%, 9 wt-%, 10 wt-%, 11 wt-%, 12 wt-%, 13 wt-%, 14 wt-%, 15 wt-%, 16 wt-%, 17 wt-%, 18 wt-%, 19 wt-%, 20 wt-%, 25 wt-%, 30 wt-%, 35 wt-%, or 40 wt-%. Without limiting the scope of invention, the numeric ranges are inclusive of the numbers defining the range and include each integer within the defined range.

Carboxylic Acid

The present invention includes a carboxylic acid with the peracid composition and hydrogen peroxide. A carboxylic acid includes any compound of the formula R—(COOH)$_n$ in which R can be hydrogen, alkyl, alkenyl, alkyne, acylic, alicyclic group, aryl, heteroaryl, or heterocylic group, and n is 1, 2, or 3. Preferably R includes hydrogen, alkyl, or alkenyl. The terms "alkyl," "alkenyl," "alkyne," "acylic," "alicyclic group," "aryl," "heteroaryl," and "heterocyclic group" are as defined above with respect to peracids.

Examples of suitable carboxylic acids according to the equilibrium systems of peracids according to the invention include a variety monocarboxylic acids, dicarboxylic acids, and tricarboxylic acids. Monocarboxylic acids include, for example, formic acid, acetic acid, propanoic acid, butanoic acid, pentanoic acid, hexanoic acid, heptanoic acid, octanoic acid, nonanoic acid, decanoic acid, undecanoic acid, dodecanoic acid, glycolic acid, lactic acid, salicylic acid, acetylsalicylic acid, mandelic acid, etc. Dicarboxylic acids include, for example, adipic acid, fumaric acid, glutaric acid, maleic acid, succinic acid, malic acid, tartaric acid, etc. Tricarboxylic acids include, for example, citric acid, trimellitic acid, isocitric acid, agaicic acid, etc.

In an aspect of the invention, a particularly well suited carboxylic acid is water soluble such as formic acid, acetic acid, propionic acid, butanoic acid, lactic acid, glycolic acid, citric acid, mandelic acid, glutaric acid, maleic acid, malic acid, adipic acid, succinic acid, tartaric acid, etc. Preferably a composition of the invention includes acetic acid, octanoic acid, or propionic acid, lactic acid, heptanoic acid, octanoic acid, or nonanoic acid. Additional examples of suitable carboxylic acids are employed in sulfoperoxycarboxylic acid or sulfonated peracid systems, which are disclosed in U.S. Pat. No. 8,344,026, and U.S. Patent Publication Nos. 2010/0048730 and 2012/0052134, each of which are herein incorporated by reference in their entirety.

Any suitable $C_1$-$C_{22}$ carboxylic acid can be used in the present compositions. In some embodiments, the $C_1$-$C_{22}$ carboxylic acid is a $C_2$-$C_{20}$ carboxylic acid. In other embodiments, the $C_1$-$C_{22}$ carboxylic acid is a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$ carboxylic acid. In still other embodiments, the $C_1$-$C_{22}$ carboxylic acid comprises acetic acid, octanoic acid and/or sulfonated oleic acid.

The $C_1$-$C_{22}$ carboxylic acid can be used at any suitable concentration. In some embodiments, the $C_1$-$C_{22}$ carboxylic acid has a concentration in an equilibrium composition from about 0.1 wt-% to about 90 wt-%. In other embodiments, the $C_1$-$C_{22}$ carboxylic acid has a concentration from about 1 wt-% to about 80 wt-%. In still other embodiments, the $C_1$-$C_{22}$ carboxylic acid has a concentration at about 1 wt-% to about 50 wt-%. Without limiting the scope of invention, the numeric ranges are inclusive of the numbers defining the range and include each integer within the defined range.

Hydrogen Peroxide

The present invention includes hydrogen peroxide. Hydrogen peroxide, $H_2O_2$, provides the advantages of having a high ratio of active oxygen because of its low molecular weight (34.014 g/mole) and being compatible with numerous substances that can be treated by methods of the invention because it is a weakly acidic, clear, and colorless liquid. Another advantage of hydrogen peroxide is that it decomposes into water and oxygen. It is advantageous to have these decomposition products because they are generally compatible with substances being treated. For example, the decomposition products are generally compatible with metallic substance (e.g., substantially noncorrosive) and are generally innocuous to incidental contact and are environmentally friendly.

In one aspect of the invention, hydrogen peroxide is initially in an antimicrobial peracid composition in an amount effective for maintaining an equilibrium between a carboxylic acid, hydrogen peroxide, and a peracid. The amount of hydrogen peroxide should not exceed an amount that would adversely affect the antimicrobial activity of a composition of the invention. In further aspects of the invention, hydrogen peroxide concentration can be significantly reduced within an antimicrobial peracid composition. In some aspects, an advantage of minimizing the concentration of hydrogen peroxide is that antimicrobial activity of a composition of the invention is improved as compared to conventional equilibrium peracid compositions.

The hydrogen peroxide can be used at any suitable concentration. In some embodiments, a concentrated equilibrium composition has a concentration of hydrogen peroxide from about 0.5 wt-% to about 90 wt-%, or from about 1 wt-% to about 90 wt-%. In still other embodiments, the hydrogen peroxide has a concentration from about 1 wt-% to about 80 wt-%, from about 1 wt-% to about 50 wt-%. Without limiting the scope of invention, the numeric ranges are inclusive of the numbers defining the range and include each integer within the defined range.

Beneficially, in some aspects of the invention, stabilized compositions and methods of the invention using the same equilibrium peracid compositions, are not reliant and/or limited according to any particular ratio of hydrogen peroxide to peracid for such enhanced stability. Instead, it is unexpected that the stabilizing agent disclosed for use in certain aspects of the claimed invention (e.g. DPA) is suitable for providing peracid stability under high acidity/mineral acid conditions. This represents a significant improvement over the prior art, wherein DPA is an optional peracid stabilizing agent for low hydrogen peroxide containing peracid compositions. See e.g. U.S. Publication No. 2010/021558, which is herein incorporated by reference in its entirety.

Mineral Acid

In some embodiments, the present composition is a strongly acidic peracid. In some aspects the peracid composition has a use solution pH of 4 or less, and preferably has a use solution pH of 3 or less. In some embodiments, the present composition includes an inorganic acid. In preferred embodiments, the present composition includes a mineral acid.

Particularly suitable mineral acids include sulfuric acid ($H_2SO_4$), hydrogen sulfate, nitric acid, sulfamic acid and sulfonic acids both alkyl and aryl, in particular methane sulfonic acid and dodecylbenzene, toluene, xylene, naphthalene and cumene sulfonic acid and/or phosphoric acid ($H_3PO_4$). Additional phosphonic acids which may be used according to the invention include, for example, aminotrimethylene phosphonic acid, ethylene diamin tetramethylene phosphonic acid, hexamethylene diamin tetramethylene phosphonic acid, diethylene triamin tetramethylene phosphonic acid, and 1-hydroxyethylidene-1,1-diphosphonic acid (HEDP).

In a further aspect, the acids suitable for use include are not limited to mineral acids. Instead, acids suitable for use include strong acids, which are defined as those with a pKa near or below the lower pKa of HEDP which may cause significant protonation of the HEDP and other phosphate and phosphonate stabilizers and thus diminish their ability to stabilize the peracid chemistries. Additional description of mineral acids for use in peracid compositions is disclosed in WO 91/07375, which is herein incorporated by reference in its entirety.

In an aspect of the invention, the mineral acid providing the strong acidity of the peracid compositions can be used at any suitable concentration. In some embodiments, a concentrated equilibrium composition has a concentration of the mineral acid from about 0.5 wt-% to about 50 wt-%, or from about 1 wt-% to about 50 wt-%. In still other embodiments, the mineral acid has a concentration from about 1 wt-% to about 20 wt-%, or more preferably from about 5 wt-% to about 20 wt-%. Without limiting the scope of invention, the numeric ranges are inclusive of the numbers defining the range and include each integer within the defined range.

Fluorescent Active Compound

The present composition is a strongly acidic equilibrium peracid containing a fluorescent active compound that is stable in the peracid compositions according to the invention. In an aspect, the fluorescent active compound is formulated directly into the equilibrium peracid composition, instead of contained in a two or more part system (e.g. peracid precursors or preformed peracids with a fluorescent active compound added prior to use and having short stability). In additional aspects, the fluorescent active compound is further stable in and suitable for use in other peracid and/or strongly oxidant systems/compositions, including compositions in concentrate and/or use solutions at both acidic and alkaline pHs. For example, in some aspects, the fluorescent active compound is further stable in highly acidic compositions (e.g. cleaning and sanitizing compositions) and caustic compositions (e.g. laundry compositions). In further aspects, the fluorescent active compound is further stable in strongly oxidant systems (often employed for sanitizing compositions), such as chlorine.

In some aspects, the fluorescent active compound may be an inert component of the composition (e.g. sanitizing compositions). In other aspects, the fluorescent active compound is an active component of the composition (e.g. cleaning compositions). In an aspect, the fluorescent active compound is an aryl sulfonate. In other aspects, the fluorescent active compound is an alkyl aryl sulfonate. In further aspects, the fluorescent active compound is an aromatic ring with a hydrophilic group (e.g. sulfonate, carboxylic). Without being limited to a particular theory or mechanism of the invention, the inclusion of the hydrophilic group of the aromatic ring beneficially results in the compatibility of the fluorescent active compound with the peracid composition.

Exemplary suitable alkyl aryl sulfonates that can be used in the compositions as fluorescent active compounds can have an alkyl group that contains 0 to 16 carbon atoms and the aryl group can be at least one of benzene, diphenyl oxide, and/or naphthalene. A suitable alkyl aryl sulfonate includes linear alkyl benzene sulfonate. A suitable linear alkyl benzene sulfonate includes linear dodecyl benzyl sulfonate that can be provided as an acid that is neutralized to form the sulfonate. Additional suitable alkyl aryl sulfonates include benzene sulfonate, toluene sulfonate, xylene sulfonate, cumene sulfonate, diphenyl oxide disulfonate, naphthalene sulfonate and naphthalene disulfonates, Additional suitable aromatic rings having a hydrophilic group are shown in the following exemplary formulas:

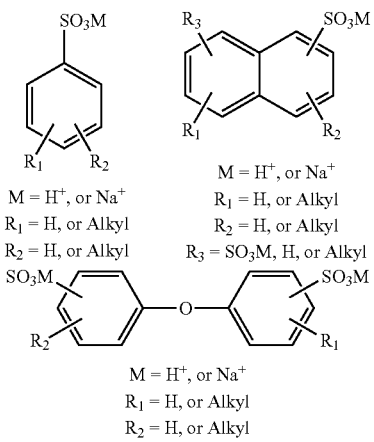

In an aspect, the fluorescent active compound is sodium xylene sulfonate (SXS), such as is commercially available from the Stepan Company, and/or sodium cumene sulfonate (SCS), such as is commercially available from AkzoNobel. In an aspect, the fluorescent active compound is sodium alkyl diphenyl disulfonate, such as commercially available from the Dow Company as Dowfax, such as Dowfax 2A1. In an aspect, the fluorescent active compound is sodium naphthalene sulfonate and/or disodium naphthalene disulfonate, and or alkyl naphthalene sulfonate, such as commercially available from AkzoNobel as PetroLBA.

In an aspect, the fluorescent active compound is suitable for indirect food use. In a further aspect, the fluorescent active compound is suitable for more than only visual assessment of peracid concentrations (e.g. UV light source to confirm on a dry substrate a disinfectant was applied). Instead, the fluorescent active compounds are suitable for dose quantification by optical measurement.

Additional fluorescent tracers that may have applications of use according to the invention are commercially available under the trade name TRASAR® (Nalco Company® (Naperville, Ill.)) and/or may be synthesized using techniques known to persons of ordinary skill in the art of organic chemistry.

In an aspect of the invention, fluorescent active compound can be used at any suitable concentration. In some embodiments, a concentrated equilibrium composition has a concentration of the fluorescent active compound from about 0.001 wt-% to about 10 wt-%, or from about 0.1 wt-% to about 10 wt-%. In still other embodiments, the fluorescent active compound has a concentration from about 0.5 wt-% to about 7.5 wt-%, or more preferably from about 1 wt-% to about 5 wt-%. Without limiting the scope of invention, the numeric ranges are inclusive of the numbers defining the range and include each integer within the defined range.

Additional Functional Ingredients

In some embodiments, the present composition can further comprise additional functional ingredients. In some embodiments, the highly acidic peracid composition including the fluorescent active compound, mineral acid, peroxycarboxylic acid, carboxylic acid, hydrogen peroxide and water make up a large amount, or even substantially all of the total weight of the peracid compositions. For example, in some embodiments few or no additional functional ingredients are disposed therein.

In other embodiments, additional functional ingredients may be included in the compositions. The functional ingredients provide desired properties and functionalities to the compositions. For the purpose of this application, the term "functional ingredient" includes a material that when dispersed or dissolved in a use and/or concentrate solution, such as an aqueous solution, provides a beneficial property in a particular use. Some particular examples of functional materials are discussed in more detail below, although the particular materials discussed are given by way of example only, and that a broad variety of other functional ingredients may be used. In some aspects, the compositions may include defoaming agents, surfactants, stabilizing agents, additional antimicrobial agents, anti-redeposition agents, bleaching agents, solubility modifiers, dispersants, rinse aids, metal protecting agents, stabilizing agents, corrosion inhibitors, fragrances and/or dyes, rheology modifiers or thickeners, hydrotropes or couplers, buffers, solvents and the like. In preferred embodiments, the compositions further include a peracid stabilizing agent. In additional preferred embodiments, the compositions do not include phosphonic acid based stabilizers (e.g. pyrophosphoric acids and/or salts thereof, HEDP, $(H_{n+2}PnO_{3n+1})$). In further preferred embodiments, the compositions further include substances that aid in the solubilization of the stabilizing agent(s), including for example, hydrotropes and/or other solvents. In still further aspects, the compositions include low foaming surfactants, such as anionic surfactants and nonionic surfactants, and a defoaming agent. In further aspects, the composition may utilize alternative hydrotropes for solubilization of the stabilizing agent, including for example, n-octanesulfonate, a xylene sulfonate, a naphthalene sulfonate, ethylhexyl sulfate, lauryl sulfate, an amine oxide, etc.

Peracid Stabilizing Agent

A peracid stabilizing agent or agents may be included in compositions according to the invention. Beneficially, the peracid stabilizing agent(s) prevents the decomposition of peracid in an equilibrium peracid composition. In addition, peracid stabilizing agent(s) prevent an equilibrium peracid composition from exceeding reaching their self-accelerating decomposition temperatures (SADT). The use of the peracid stabilizing agent beneficially stabilizes highly acidity, equilibrium peracids, including mixed peracid compositions, as well as extreme chemistries with problematic high peracid to hydrogen peroxide ratios. By elevating the SADTs of the compositions the stabilizers provide significant safety benefits for transportation and storage of the compositions. In some aspects, the stabilizing agents delay or prevent the composition from meeting its native SADT. In an aspect of the invention, the stabilizing agent is a pyridine carboxylic acid compound. Pyridine carboxylic acids include dipicolinic acids, including for example, 2,6-pyridinedicarboxylic acid (DPA). In a further aspect, the stabilizing agent is a picolinic acid, or a salt thereof.

In an aspect of the invention, the stabilizing agent is a picolinic acid or a compound having the following Formula (IA):

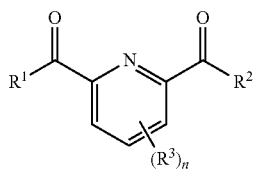

wherein $R^1$ is OH or $-NR^{1a}R^{1b}$, wherein $R^{1a}$ and $R^{1b}$ are independently hydrogen or $(C_1-C_6)$alkyl; $R^2$ is OH or $-NR^{2a}R^{2b}$, wherein $R^{2a}$ and $R^{2b}$ are independently hydrogen or $(C_1-C_6)$alkyl; each $R^3$ is independently $(C_1-C_6)$alkyl, $(C_2-C_6)$alkenyl or $(C_2-C_6)$alkynyl; and n is a number from zero to 3; or a salt thereof.

In a further aspect of the invention, the peracid stabilizing agent is a compound having the following Formula (IB):

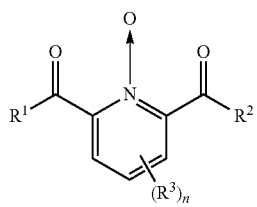

wherein $R^1$ is OH or $-NR^{1a}R^{1b}$, wherein $R^{1a}$ and $R^{1b}$ are independently hydrogen or $(C_1-C_6)$alkyl; $R^2$ is OH or $-NR^{2a}R^{2b}$, wherein $R^{2a}$ and $R^{2b}$ are independently hydrogen or $(C_1-C_6)$alkyl; each $R^3$ is independently $(C_1-C_6)$alkyl, $(C_2-C_6)$alkenyl or $(C_2-C_6)$alkynyl; and n is a number from zero to 3; or a salt thereof.

In a preferred aspect, the peracid stabilizing agent is dipicolinic acid (picolinic acid, 2,6-Pyridinedicarboxylic acid) and provides stabilization for high mineral content peracids, wherein the peracid does not exceed its SADT.

Dipicolinic acid has been used as a stabilizer for peracid compositions, such as disclosed in WO 91/07375 and U.S. Pat. No. 2,609,391, which are herein incorporated by reference in their entirety. However, use of such DPA stabilizer for peracid compositions has not previously been capable of formulating strongly acidic peracid compositions with sufficiently constrained SADT for a particular peracid compositions. Beneficially, according to the invention, the stabilized highly acidic peracid compositions having a use solution pH of about 4 or less (or preferably 3 or less) resulting in the SADT of the composition increasing to at least about 45° C. during transportation, or at least about 50° C. during transportation. In addition, to the benefits afforded to the SADT of the peracid compositions according to the invention, the stabilizing agents provide significantly improved stabilization in comparison to conventional phosphate stabilizers, such as Dequest 2010.

In a further aspect, the stabilizing agent may be combined with additional conventional stabilizing agents, e.g. a phosphonate based stabilizer, such as disclosed in U.S. application Ser. No. 13/785,044 (Ecolab 2981US01) titled "Efficient Stabilizer in Controlling Self Accelerated Decomposition Temperature of Peroxycarboxylic Acid Compositions with Mineral Acids," which is herein incorporated by reference in its entirety.

Stabilizing agents may be present in amounts sufficient to provide the intended stabilizing benefits, namely achieving the desired shelf life, and elevating the SADT of the highly acidic peroxycarboxylic acid compositions having a use solution pH of below at least 4, preferably below at least 3. As the property of the composition will vary depending upon the acidity of the particular peracid composition according to the invention, such peracid stabilizing agents may be present in a concentrated equilibrium peracid composition in amounts from about 0.001 wt-% to about 25 wt-%, 0.01 wt-% to about 10 wt-%, and more preferably from about 0.01 wt-% to about 1 wt-%. Without limiting the scope of invention, the numeric ranges are inclusive of the numbers defining the range and include each integer within the defined range.

Defoaming Agent

The present invention may include a defoaming agent. Defoaming agents suitable for use in the peroxycarboxylic acid compositions according to the invention are compatible with the highly acidic peracid compositions and anionic and/or nonionic surfactants which may be employed in the peracid compositions. The defoaming agents suitable for use in the peroxycarboxylic acid compositions according to the invention, maintain a low foam profile under various water conditions, preferably under deionized or soft water conditions, and/or under mechanical action. In a still further aspect, the defoaming agents are compatible with surfactants, preferably anionic surfactants, to achieve critical performance such as coupling/wetting, improved material compatibility and enhanced biocidal efficacy. In preferred aspects, the defoaming agent provides a synergistic biocidal efficacy.

In an aspect of the invention, the defoaming agent is a metal salt, including for example, aluminum, magnesium, calcium, zinc and/or other rare earth metal salts. In a preferred aspect, the defoaming agent is a cation with high charge density, such as $Fe^{3+}$, $Al^{3+}$ and $La^{3+}$. In a preferred aspect, the defoaming agent is aluminum sulfate.

In an aspect, the defoaming agent is not a transition metal compound, which are incompatible with the highly acidic equilibrium peracid compositions according to the invention.

In some embodiments, the compositions of the present invention can include antifoaming agents or defoamers which are of food grade quality given the application of the method of the invention.

In a further embodiment, the compositions of the present invention can include defoaming agents which are stable in acid environments (e.g. the peracid compositions containing a mineral acid and having a use solution pH of about 4 or less) and/or are oxidatively stable.

In an aspect of the invention, the defoaming agent can be used at any suitable concentration to provide defoaming with the surfactants according to the invention and to provide synergistic biocidal efficacy. In some embodiments, a concentrated equilibrium composition has a concentration of the a defoaming agent from about 0.001 wt-% to about 10 wt-%, or from about 0.1 wt-% to about 5 wt-%. In still other embodiments, the defoaming agent has a concentration from about 0.1 wt-% to about 1 wt-%. Without limiting the scope of invention, the numeric ranges are inclusive of the numbers defining the range and include each integer within the defined range.

Surfactants

In some embodiments, the compositions of the present invention include a surfactant. Surfactants suitable for use with the compositions of the present invention include, but are not limited to nonionic surfactants and/or anionic surfactants. Preferably, a low foaming anionic surfactant is included in the peroxycarboxylic acid compositions. Beneficially, according to embodiments of the invention, the use of the defoaming agent (e.g. aluminum sulfate) in combination with the surfactant overcomes the foaming issues that are known to result from the use of conventional low-foaming surfactants in peroxycarboxylic acid compositions, especially in deionized or soft water.

In some embodiments, the compositions of the present invention include about 0 wt-% to about 40 wt-% of a surfactant. In other embodiments the compositions of the present invention include about 0.1 wt-% to about 40 wt-% of a surfactant, preferably from about 0.1 wt-% to about 25 wt-% of a surfactant, and more preferably from about 1 wt-% to about 20 wt-% of a surfactant.

Anionic Surfactants

Preferably, surface active substances which are categorized as anionics because the charge on the hydrophobe is negative are utilized according to the present invention; or surfactants in which the hydrophobic section of the molecule carries no charge unless the pH is elevated to neutrality or above (e.g. carboxylic acids). Carboxylate, sulfonate, sulfate and phosphate are the polar (hydrophilic) solubilizing groups found in anionic surfactants. Of the cations (counter ions) associated with these polar groups, sodium, lithium and potassium impart water solubility; ammonium and substituted ammonium ions provide both water and oil solubility; and, calcium, barium, and magnesium promote oil solubility. As those skilled in the art understand, anionics are excellent detersive surfactants and are therefore favored additions to heavy duty detergent compositions.

Anionic sulfate surfactants suitable for use in the present compositions include alkyl ether sulfates, alkyl sulfates, the linear and branched primary and secondary alkyl sulfates, alkyl ethoxysulfates, fatty oleyl glycerol sulfates, alkyl phenol ethylene oxide ether sulfates, the $C_5$-$C_{17}$ acyl-N—($C_1$-$C_4$ alkyl) and —N—($C_1$-$C_2$ hydroxyalkyl) glucamine sulfates, and sulfates of alkylpolysaccharides such as the sulfates of alkylpolyglucoside, and the like. Also included are the alkyl sulfates, alkyl poly(ethyleneoxy) ether sulfates and aromatic poly(ethyleneoxy) sulfates such as the sulfates or condensation products of ethylene oxide and nonyl phenol (usually having 1 to 6 oxyethylene groups per molecule).

Anionic sulfonate surfactants suitable for use in the present compositions also include alkyl sulfonates, the linear and branched primary and secondary alkyl sulfonates, and the aromatic sulfonates with or without substituents.

Anionic carboxylate surfactants suitable for use in the present compositions include carboxylic acids (and salts), such as alkanoic acids (and alkanoates), sulfonated fatty acids (e.g. carboxylic acids), such as sulfonated oleic acid, ester carboxylic acids (e.g. alkyl succinates), ether carboxylic acids, and the like. Such carboxylates include alkyl ethoxy carboxylates, alkyl aryl ethoxy carboxylates, alkyl polyethoxy polycarboxylate surfactants and soaps (e.g. alkyl carboxyls). Secondary carboxylates useful in the present compositions include those which contain a carboxyl unit connected to a secondary carbon. The secondary carbon can be in a ring structure, e.g. as in p-octyl benzoic acid, or as in alkyl-substituted cyclohexyl carboxylates. The secondary carboxylate surfactants typically contain no ether linkages, no ester linkages and no hydroxyl groups. Further, they typically lack nitrogen atoms in the head-group (amphiphilic portion). Suitable secondary soap surfactants typically contain 11-13 total carbon atoms, although more carbons atoms (e.g., up to 16) can be present. Suitable carboxylates also include acylamino acids (and salts), such as acylgluamates, acyl peptides, sarcosinates (e.g. N-acyl sarcosinates), taurates (e.g. N-acyl taurates and fatty acid amides of methyl tauride), and the like.

Suitable anionic surfactants include alkyl or alkylaryl ethoxy carboxylates of the following formula:

$$R—O—(CH_2CH_2O)_n(CH_2)_m—CO_2X \qquad (3)$$

in which R is a $C_8$ to $C_{22}$ alkyl group or

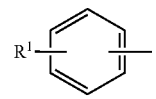

in which $R^1$ is a $C_4$-$C_{16}$ alkyl group; n is an integer of 1-20; m is an integer of 1-3; and X is a counter ion, such as hydrogen, sodium, potassium, lithium, ammonium, or an amine salt such as monoethanolamine, diethanolamine or triethanolamine. In some embodiments, n is an integer of 4 to 10 and m is 1. In some embodiments, R is a $C_8$-$C_{16}$ alkyl group. In some embodiments, R is a $C_{12}$-$C_{14}$ alkyl group, n is 4, and m is 1.

In other embodiments, R is

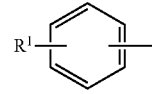

and $R^1$ is a $C_6$-$C_{12}$ alkyl group. In still yet other embodiments, $R^1$ is a $C_9$ alkyl group, n is 10 and m is 1.

Such alkyl and alkylaryl ethoxy carboxylates are commercially available. These ethoxy carboxylates are typically available as the acid forms, which can be readily converted to the anionic or salt form. Commercially available carboxylates include, Neodox 23-4, a $C_{12-13}$ alkyl polyethoxy (4) carboxylic acid (Shell Chemical), and Emcol CNP-110, a $C_9$ alkylaryl polyethoxy (10) carboxylic acid (Witco Chemical). Carboxylates are also available from Clariant, e.g. the product Sandopan® DTC, a $C_{13}$ alkyl polyethoxy (7) carboxylic acid.

Nonionic Surfactants

Useful nonionic surfactants are generally characterized by the presence of an organic hydrophobic group and an organic hydrophilic group and are typically produced by the condensation of an organic aliphatic, alkyl aromatic or polyoxyalkylene hydrophobic compound with a hydrophilic alkaline oxide moiety which in common practice is ethylene oxide or a polyhydration product thereof, polyethylene glycol. Practically any hydrophobic compound having a hydroxyl, carboxyl, amino, or amido group with a reactive hydrogen atom can be condensed with ethylene oxide, or its polyhydration adducts, or its mixtures with alkoxylenes such as propylene oxide to form a nonionic surface-active agent. The length of the hydrophilic polyoxyalkylene moiety which is condensed with any particular hydrophobic compound can be readily adjusted to yield a water dispersible or water soluble compound having the desired degree of balance between hydrophilic and hydrophobic properties. Useful nonionic surfactants include:

1. Block polyoxypropylene-polyoxyethylene polymeric compounds based upon propylene glycol, ethylene glycol, glycerol, trimethylolpropane, and ethylenediamine as the initiator reactive hydrogen compound. Examples of polymeric compounds made from a sequential propoxylation and ethoxylation of initiator are commercially available under the trade names Pluronic® and Tetronic® manufactured by BASF Corp. Pluronic® compounds are difunctional (two reactive hydrogens) compounds formed by condensing ethylene oxide with a hydrophobic base formed by the addition of propylene oxide to the two hydroxyl groups of propylene glycol. This hydrophobic portion of the molecule weighs from about 1,000 to about 4,000. Ethylene oxide is then added to sandwich this hydrophobe between hydrophilic groups, controlled by length to constitute from about 10% by weight to about 80% by weight of the final molecule. Tetronic® compounds are tetra-flinctional block copolymers derived from the sequential addition of propylene oxide and ethylene oxide to ethylenediamine. The molecular weight of the propylene oxide hydrotype ranges from about 500 to about 7,000; and, the hydrophile, ethylene oxide, is added to constitute from about 10% by weight to about 80% by weight of the molecule.

2. Condensation products of one mole of alkyl phenol wherein the alkyl chain, of straight chain or branched chain configuration, or of single or dual alkyl constituent, contains from about 8 to about 18 carbon atoms with from about 3 to about 50 moles of ethylene oxide. The alkyl group can, for example, be represented by diisobutylene, di-amyl, polymerized propylene, iso-octyl, nonyl, and di-nonyl. These surfactants can be polyethylene, polypropylene, and polybutylene oxide condensates of alkyl phenols. Examples of commercial compounds of this chemistry are available on the market under the trade names Igepal® manufactured by Rhone-Poulenc and Triton® manufactured by Union Carbide.

3. Condensation products of one mole of a saturated or unsaturated, straight or branched chain alcohol having from about 6 to about 24 carbon atoms with from about 3 to about 50 moles of ethylene oxide. The alcohol moiety can consist of mixtures of alcohols in the above delineated carbon range or it can consist of an alcohol having a specific number of carbon atoms within this range. Examples of like commercial surfactant are available under the trade names Neodol™ manufactured by Shell Chemical Co. and Alfonic™ manufactured by Vista Chemical Co.

4. Condensation products of one mole of saturated or unsaturated, straight or branched chain carboxylic acid having from about 8 to about 18 carbon atoms with from about 6 to about 50 moles of ethylene oxide. The acid moiety can consist of mixtures of acids in the above defined carbon atoms range or it can consist of an acid having a specific number of carbon atoms within the range. Examples of commercial compounds of this chemistry are available on the market under the trade names Nopalcol™ manufactured by Henkel Corporation and Lipopeg™ manufactured by Lipo Chemicals, Inc.

In addition to ethoxylated carboxylic acids, commonly called polyethylene glycol esters, other alkanoic acid esters formed by reaction with glycerides, glycerin, and polyhydric (saccharide or sorbitan/sorbitol) alcohols have application in this invention for specialized embodiments, particularly indirect food additive applications. All of these ester moieties have one or more reactive hydrogen sites on their molecule which can undergo further acylation or ethylene oxide (alkoxide) addition to control the hydrophilicity of these substances. Care must be exercised when adding these fatty ester or acylated carbohydrates to compositions of the present invention containing amylase and/or lipase enzymes because of potential incompatibility.

Examples of nonionic low foaming surfactants include:

5. Compounds from (1) which are modified, essentially reversed, by adding ethylene oxide to ethylene glycol to provide a hydrophile of designated molecular weight; and, then adding propylene oxide to obtain hydrophobic blocks on the outside (ends) of the molecule. The hydrophobic portion of the molecule weighs from about 1,000 to about 3,100 with the central hydrophile including 10% by weight to about 80% by weight of the final molecule. These reverse Pluronics™ are manufactured by BASF Corporation under the trade name Pluronic™ R surfactants. Likewise, the Tetronic™ R surfactants are produced by BASF Corporation by the sequential addition of ethylene oxide and propylene oxide to ethylenediamine. The hydrophobic portion of the molecule weighs from about 2,100 to about 6,700 with the central hydrophile including 10% by weight to 80% by weight of the final molecule.

6. Compounds from groups (1), (2), (3) and (4) which are modified by "capping" or "end blocking" the terminal hydroxy group or groups (of multi-functional moieties) to reduce foaming by reaction with a small hydrophobic molecule such as propylene oxide, butylene oxide, benzyl chloride; and, short chain fatty acids, alcohols or alkyl halides containing from 1 to about 5 carbon atoms; and mixtures thereof. Also included are reactants such as thionyl chloride which convert terminal hydroxy groups to a chloride group. Such modifications to the terminal hydroxy group may lead to all-block, block-heteric, heteric-block or all-heteric nonionics.

Additional examples of effective low foaming nonionics include:

7. The alkylphenoxypolyethoxyalkanols of U.S. Pat. No. 2,903,486 issued Sep. 8, 1959 to Brown et al. and represented by the formula

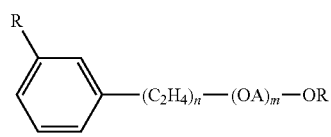

in which R is an alkyl group of 8 to 9 carbon atoms, A is an alkylene chain of 3 to 4 carbon atoms, n is an integer of 7 to 16, and m is an integer of 1 to 10.

The polyalkylene glycol condensates of U.S. Pat. No. 3,048,548 issued Aug. 7, 1962 to Martin et al. having alternating hydrophilic oxyethylene chains and hydrophobic oxypropylene chains where the weight of the terminal hydrophobic chains, the weight of the middle hydrophobic unit and the weight of the linking hydrophilic units each represent about one-third of the condensate.

The defoaming nonionic surfactants disclosed in U.S. Pat. No. 3,382,178 issued May 7, 1968 to Lissant et al. having the general formula $Z[(OR)_nOH]_z$ wherein Z is alkoxylatable material, R is a radical derived from an alkaline oxide which can be ethylene and propylene and n is an integer from, for example, 10 to 2,000 or more and z is an integer determined by the number of reactive oxyalkylatable groups.

The conjugated polyoxyalkylene compounds described in U.S. Pat. No. 2,677,700, issued May 4, 1954 to Jackson et al. corresponding to the formula $Y(C_3H_6O)_n(C_2H_4O)_mH$ wherein Y is the residue of organic compound having from about 1 to 6 carbon atoms and one reactive hydrogen atom, n has an average value of at least about 6.4, as determined by hydroxyl number and m has a value such that the oxyethylene portion constitutes about 10% to about 90% by weight of the molecule.

The conjugated polyoxyalkylene compounds described in U.S. Pat. No. 2,674,619, issued Apr. 6, 1954 to Lundsted et al. having the formula $Y[(C_3H_6O)_n(C_2H_4O)_mH]_x$ wherein Y is the residue of an organic compound having from about 2 to 6 carbon atoms and containing x reactive hydrogen atoms in which x has a value of at least about 2, n has a value such that the molecular weight of the polyoxypropylene hydrophobic base is at least about 900 and m has value such that the oxyethylene content of the molecule is from about 10% to about 90% by weight. Compounds falling within the scope of the definition for Y include, for example, propylene glycol, glycerine, pentaerythritol, trimethylolpropane, ethylenediamine and the like. The oxypropylene chains optionally, but advantageously, contain small amounts of ethylene oxide and the oxyethylene chains also optionally, but advantageously, contain small amounts of propylene oxide.

Additional conjugated polyoxyalkylene surface-active agents which are advantageously used in the compositions of this invention correspond to the formula: $P[(C_3H_6O)_n(C_2H_4O)_mH]_x$ wherein P is the residue of an organic compound having from about 8 to 18 carbon atoms and containing x reactive hydrogen atoms in which x has a value of 1 or 2, n has a value such that the molecular weight of the polyoxyethylene portion is at least about 44 and m has a value such that the oxypropylene content of the molecule is from about 10% to about 90% by weight. In either case the oxypropylene chains may contain optionally, but advantageously, small amounts of ethylene oxide and the oxyethylene chains may contain also optionally, but advantageously, small amounts of propylene oxide.

8. Polyhydroxy fatty acid amide surfactants suitable for use in the present compositions include those having the structural formula $R_2CON_{R1}Z$ in which: R1 is H, $C_1$-$C_4$ hydrocarbyl, 2-hydroxy ethyl, 2-hydroxy propyl, ethoxy, propoxy group, or a mixture thereof, $R_2$ is a $C_5$-$C_{31}$ hydrocarbyl, which can be straight-chain; and Z is a polyhydroxyhydrocarbyl having a linear hydrocarbyl chain with at least 3 hydroxyls directly connected to the chain, or an alkoxylated derivative (preferably ethoxylated or propoxylated) thereof. Z can be derived from a reducing sugar in a reductive amination reaction; such as a glycityl moiety.

9. The alkyl ethoxylate condensation products of aliphatic alcohols with from about 0 to about 25 moles of ethylene oxide are suitable for use in the present compositions. The alkyl chain of the aliphatic alcohol can either be straight or branched, primary or secondary, and generally contains from 6 to 22 carbon atoms.

10. The ethoxylated $C_6$-$C_{18}$ fatty alcohols and $C_6$-$C_{18}$ mixed ethoxylated and propoxylated fatty alcohols are suitable surfactants for use in the present compositions, particularly those that are water soluble. Suitable ethoxylated fatty alcohols include the $C_6$-Cis ethoxylated fatty alcohols with a degree of ethoxylation of from 3 to 50.

11. Suitable nonionic alkylpolysaccharide surfactants, particularly for use in the present compositions include those disclosed in U.S. Pat. No. 4,565,647, Llenado, issued Jan. 21, 1986. These surfactants include a hydrophobic group containing from about 6 to about 30 carbon atoms and a polysaccharide, e.g., a polyglycoside, hydrophilic group containing from about 1.3 to about 10 saccharide units. Any reducing saccharide containing 5 or 6 carbon atoms can be used, e.g., glucose, galactose and galactosyl moieties can be substituted for the glucosyl moieties. (Optionally the hydrophobic group is attached at the 2-, 3-, 4-, etc. positions thus giving a glucose or galactose as opposed to a glucoside or galactoside.) The intersaccharide bonds can be, e.g., between the one position of the additional saccharide units and the 2-, 3-, 4-, and/or 6-positions on the preceding saccharide units.

12. Fatty acid amide surfactants suitable for use the present compositions include those having the formula: $R_6CON(R_7)_2$ in which $R_6$ is an alkyl group containing from 7 to 21 carbon atoms and each $R_7$ is independently hydrogen, $C_1$-$C_4$ alkyl, $C_1$-$C_4$ hydroxyalkyl, or $-(C_2H_4O)xH$, where x is in the range of from 1 to 3.

13. A useful class of non-ionic surfactants include the class defined as alkoxylated amines or, most particularly, alcohol alkoxylated/aminated/alkoxylated surfactants. These non-ionic surfactants may be at least in part represented by the general formulae: $R^{20}-(PO)_sN-(EO)_tH$, $R^{20}-(PO)_sN-(EO)_tH(EO)_tH$, and $R^{20}-N(EO)_tH$; in which $R^{20}$ is an alkyl, alkenyl or other aliphatic group, or an alkyl-aryl group of from 8 to 20, preferably 12 to 14 carbon atoms, EO is oxyethylene, PO is oxypropylene, s is 1 to 20, preferably 2-5, t is 1-10, preferably 2-5, and u is 1-10, preferably 2-5. Other variations on the scope of these compounds may be represented by the alternative formula: $R^{20}-(PO)_v-N[(EO)_wH][(EO)_zH]$ in which $R^{20}$ is as defined above, v is 1 to 20 (e.g., 1, 2, 3, or 4 (preferably 2)), and w and z are independently 1-10, preferably 2-5. These compounds are represented commercially by a line of products sold by Huntsman Chemicals as nonionic surfactants. A preferred chemical of this class includes Surfonic™ PEA 25 Amine Alkoxylate. Preferred nonionic surfactants for the compositions of the invention include alcohol alkoxylates, EO/PO block copolymers, alkylphenol alkoxylates, and the like.

The treatise *Nonionic Surfactants*, edited by Schick, M. J., Vol. 1 of the Surfactant Science Series, Marcel Dekker, Inc., New York, 1983 is an excellent reference on the wide variety of nonionic compounds generally employed in the practice of the present invention. A typical listing of nonionic classes, and species of these surfactants, is given in U.S. Pat. No. 3,929,678 issued to Laughlin and Heuring on Dec. 30, 1975. Further examples are given in "Surface Active Agents and detergents" (Vol. I and II by Schwartz, Perry and Berch).

Semi-Polar Nonionic Surfactants

The semi-polar type of nonionic surface active agents are another class of nonionic surfactant useful in compositions of the present invention. Generally, semi-polar nonionics are high foamers and foam stabilizers, which can limit their application in CIP systems. However, within compositional embodiments of this invention designed for high foam cleaning methodology, semi-polar nonionics would have immediate utility. The semi-polar nonionic surfactants include the amine oxides, phosphine oxides, sulfoxides and their alkoxylated derivatives.

14. Amine oxides are tertiary amine oxides corresponding to the general formula:

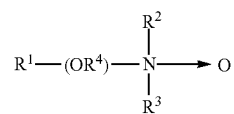

wherein the arrow is a conventional representation of a semi-polar bond; and, $R^1$, $R^2$, and $R^3$ may be aliphatic, aromatic, heterocyclic, alicyclic, or combinations thereof. Generally, for amine oxides of detergent interest, $R^1$ is an alkyl radical of from about 8 to about 24 carbon atoms; $R^2$ and $R^3$ are alkyl or hydroxyalkyl of 1-3 carbon atoms or a mixture thereof; $R^2$ and $R^3$ can be attached to each other, e.g. through an oxygen or nitrogen atom, to form a ring structure; $R^4$ is an alkaline or a hydroxyalkylene group containing 2 to 3 carbon atoms; and n ranges from 0 to about 20.

Useful water soluble amine oxide surfactants are selected from the coconut or tallow alkyl di-(lower alkyl) amine oxides, specific examples of which are dodecyldimethylamine oxide, tridecyldimethylamine oxide, etradecyldimethylamine oxide, pentadecyldimethylamine oxide, hexadecyldimethylamine oxide, heptadecyldimethylamine oxide, octadecyldimethylaine oxide, dodecyldipropylamine oxide, tetradecyldipropylamine oxide, hexadecyldipropylamine oxide, tetradecyldibutylamine oxide, octadecyldibutylamine oxide, bis(2-hydroxyethyl)dodecylamine oxide, bis(2-hydroxyethyl)-3-dodecoxy-1-hydroxypropylamine oxide, dimethyl-(2-hydroxydodecyl)amine oxide, 3,6,9-trioctadecyldimethylamine oxide and 3-dodecoxy-2-hydroxypropyldi-(2-hydroxyethyl)amine oxide.

Useful semi-polar nonionic surfactants also include the water soluble phosphine oxides having the following structure:

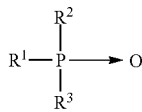

wherein the arrow is a conventional representation of a semi-polar bond; and, $R^1$ is an alkyl, alkenyl or hydroxyalkyl moiety ranging from 10 to about 24 carbon atoms in chain length; and, $R^2$ and $R^3$ are each alkyl moieties separately selected from alkyl or hydroxyalkyl groups containing 1 to 3 carbon atoms.

Examples of useful phosphine oxides include dimethyldecylphosphine oxide, dimethyltetradecylphosphine oxide, methylethyltetradecylphosphone oxide, dimethylhexadecylphosphine oxide, diethyl-2-hydroxyoctyldecylphosphine oxide, bis(2-hydroxyethyl)dodecylphosphine oxide, and bis(hydroxymethyl)tetradecylphosphine oxide.

Semi-polar nonionic surfactants useful herein also include the water soluble sulfoxide compounds which have the structure:

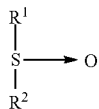

wherein the arrow is a conventional representation of a semi-polar bond; and, $R^1$ is an alkyl or hydroxyalkyl moiety of about 8 to about 28 carbon atoms, from 0 to about 5 ether linkages and from 0 to about 2 hydroxyl substituents; and $R^2$ is an alkyl moiety consisting of alkyl and hydroxyalkyl groups having 1 to 3 carbon atoms.

Useful examples of these sulfoxides include dodecyl methyl sulfoxide; 3-hydroxy tridecyl methyl sulfoxide; 3-methoxy tridecyl methyl sulfoxide; and 3-hydroxy-4-dodecoxybutyl methyl sulfoxide.

Semi-polar nonionic surfactants for the compositions of the invention include dimethyl amine oxides, such as lauryl dimethyl amine oxide, myristyl dimethyl amine oxide, cetyl dimethyl amine oxide, combinations thereof, and the like. Useful water soluble amine oxide surfactants are selected from the octyl, decyl, dodecyl, isododecyl, coconut, or tallow alkyl di-(lower alkyl) amine oxides, specific examples of which are octyldimethylamine oxide, nonyldimethylamine oxide, decyldimethylamine oxide, undecyldimethylamine oxide, dodecyldimethylamine oxide, isododecyldimethyl amine oxide, tridecyldimethylamine oxide, tetradecyldimethylamine oxide, pentadecyldimethylamine oxide, hexadecyldimethylamine oxide, heptadecyldimethylamine oxide, octadecyldimethylaine oxide, dodecyldipropylamine oxide, tetradecyldipropylamine oxide, hexadecyldipropylamine oxide, tetradecyldibutylamine oxide, octadecyldibutylamine oxide, bis(2-hydroxyethyl)dodecylamine oxide, bis(2-hydroxyethyl)-3-dodecoxy-1-hydroxypropylamine oxide, dimethyl-(2-hydroxydodecyl) amine oxide, 3,6,9-trioctadecyldimethylamine oxide and 3-dodecoxy-2-hydroxypropyldi-(2-hydroxyethyl)amine oxide.

Suitable nonionic surfactants suitable for use with the compositions of the present invention include alkoxylated surfactants. Suitable alkoxylated surfactants include EO/PO copolymers, capped EO/PO copolymers, alcohol alkoxylates, capped alcohol alkoxylates, mixtures thereof, or the like. Suitable alkoxylated surfactants for use as solvents include EO/PO block copolymers, such as the Pluronic and reverse Pluronic surfactants; alcohol alkoxylates, such as Dehypon LS-54 (R-$(EO)_5(PO)_4$) and Dehypon LS-36 (R-$(EO)_3(PO)_6$); and capped alcohol alkoxylates, such as Plurafac LF221 and Tegoten EC 11; mixtures thereof, or the like.

Methods of Monitoring and/or Determining Peracid Concentration

The methods of monitoring and/or detecting the concentrations of peracid and/or hydrogen peroxide in a use composition employing the peracid compositions of the invention provide a significant benefit of traceability, monitoring and/or measurement of such concentrations within various peroxycarboxylic acid compositions, including equilibrium peracid compositions, as well as other strong oxidizing compositions (e.g. sanitizing compositions). Previously, various inert fluorescent tracers have been used (e.g. 1,3,6,8-pyrenetetrasulfonic acid, tetrasodium salt, 2-anthracenesulfonic acid sodium salt, etc.) and are disclosed for example in U.S. Pat. No. 7,910,371, which is herein incorporated by reference in its entirety; however, these fluorescent compounds are not approved for non-rinse food contact application, and are not stable in the highly concentrated equilibrium peracid compositions and/or strongly oxidizing compositions according to the present invention.

In an aspect, the methods of the invention are suitable for use in monitoring and/or detecting the concentration of the peroxycarboxylic acid compositions that are delivered to a system and/or cleaning application. In another aspect, the methods of the invention are suitable for use in monitoring and/or detecting the concentration of the peroxycarboxylic acid compositions that are circulated within a system and/or within a cleaning application (e.g. prior to and/or during an application of use). In a still further aspect, the methods of the invention are suitable for use in monitoring and/or detecting the concentration of the peroxycarboxylic acid compositions that are stored and/or housed prior to an application of use.

In an aspect of the invention, the methods of monitoring and/or detecting the concentration of the peroxycarboxylic acid compositions are suitable for extended use due to the stability of the fluorescent active compound within the various compositions, including the equilibrium peroxycarboxylic acid compositions. Beneficially, the fluorescent active compounds are stable and can be monitoring and/or detecting according to the methods disclosed herein for at least about 180 days, preferably at least about 12 months, or greater.

The compositions according to the invention are suitable for monitoring the concentration of the peroxycarboxylic acid compositions using light absorbance or fluorescence. As one skilled in the art appreciates, the fluorescence can be measured using a variety of different and suitable techniques. For example, fluorescence emission spectroscopy (e.g. fluorometrically monitoring) on a substantially continuous basis, at least over a given time period, is one of the preferred analytical techniques according to an embodiment of this invention. One method for the continuous on-stream measuring of chemical tracers by fluorescence emission spectroscopy and other analysis methods is described in U.S. Pat. No. 4,992,380, incorporated herein by reference.

Examples of fluorometers that may be used in the practice of this invention include the Xe II and TRASAR® 8000 fluorometer (available from Nalco Company); the Hitachi F-4500 fluorometer (available from Hitachi through Hitachi Instruments Inc.); the JOBIN YVON FluoroMax-3 "SPEX" fluorometer (available from JOBIN YVON Inc.); and the Gilford Fluoro-IV spectrophotometer or the SFM 25 (available from Bio-tech Kontron through Research Instruments International). It should be appreciated that the foregoing list is not comprehensive and is intended only to show examples of representative fluorometers. Other commercially available fluorometers and modifications thereof can also be used in this invention.

In another aspect, a variety of other suitable analytical techniques may be utilized to measure the amount of fluorescent active compounds. Examples of such techniques include combined HPLC-fluorescence analysis, colorimetry analysis, ion selective electrode analysis, transition metal analysis, chemiluminescence, pulsed fluorescence measurements, and the like.

In an aspect, this allows for precise control of the peroxycarboxylic acid composition dosage. For example, the fluorescent signal of the fluorescent active compound may be used to determine the concentration of the peroxycarboxylic acid and/or hydrogen peroxide in a cleaning and/or sanitizing system. In an aspect, the fluorescent signal of the fluorescent active compound is then used to determine whether the desired amount of the peroxycarboxylic acid and/or hydrogen peroxide is present in a concentrate and/or use solution. As a result, the feed of the concentrate and/or use solution of the compositions according to the invention can then be adjusted.

As one skilled in the art ascertains, the fluorescent active compound is used to detect fluorescence at one or more locations within a storage container, cleaning system, water system, piping, or the like that is containing/housing the peroxycarboxylic acid compositions (or use solutions thereof) according to the invention. In an aspect, the fluorescence is correlated with the concentration of the peroxycarboxylic acid and/or hydrogen peroxide concentration of the tested solution. Optionally, corrective action may be taken.

In an aspect, the methods of the invention include providing one or more fluorometers and locating said fluorometer(s) in position to sample a use solution of the concentrated peroxycarboxylic acid compositions according to the invention. In an aspect, the fluorometer is placed in or along a feed line delivering the peroxycarboxylic acid compositions to a cleaning application, such as for example a ware wash machine and/or CIP application.

The compositions according to the invention are also suitable for use in monitoring by conductivity and/or an optical sensor (may also be referred to as an optical cell and/or an optical detector), such as is disclosed, for example, in the methods and/or apparatuses in U.S. Patent Publication Nos. 2012/014912, 2012/0085931, 2011/0320133, 2011/0260079, 2010/0328476, 20090150106, 20090150086 and 2009/0147822, and U.S. Pat. Nos. 8,143,070, 8,119,412, 8,076,155, 8,076,154, and 7,169,236, each of which is herein incorporated by reference in its entirety. The apparatuses, sensors and/or cells suitable for measuring or monitoring peroxycarboxylic acid and/or hydrogen peroxide content within a use solution are not limited according to the invention. Beneficially, any such apparatuses, sensors and/or cells which are compatible with the highly acidic peroxycarboxylic acid compositions according to the invention may be employed.

In an aspect, the methods of the invention include providing one or more optical sensors/cells and locating said optical sensors/cells in position to measure a sample of a use solution of the concentrated peroxycarboxylic acid compositions according to the invention. In an aspect, the optical sensor/cell is placed in or along a feed line delivering the peroxycarboxylic acid compositions to a cleaning application, such as for example a ware wash machine and/or CIP application.

In an aspect, the methods of the invention include determining the concentrations of peracid and/or hydrogen peroxide in a use composition as a result of the compositions formulated to include a fluorescent active compound. In an aspect of the invention, the monitoring includes determining whether a concentration of peracid satisfies at least a minimum threshold concentration. In another aspect of the invention, the monitoring includes determining when the concentration of hydrogen peroxide exceeds a maximum threshold concentration. Various types of apparatus and methods for determining the concentration of peracid and/or hydrogen peroxide in a use composition may employ the compositions according to the invention.

In an aspect, a detector is used to determine the concentrations of peracid and/or hydrogen peroxide in a use composition. In an aspect of the invention, a detector measures at least one characteristic of the sample mixture indicative of the concentrations of peracid and/or hydrogen peroxide in the use composition, such as the fluorescent active compound.

The measurements obtained by detector may be referred to herein as "response data." In an aspect, a processor determines the concentration of peracid and/or hydrogen peroxide in a use composition based on the response data. In one embodiment, the detector is an optical sensor/cell/detector that measures the transmittance and/or the absorbance of the sample. In that embodiment, the response data may be the optical transmittance data or optical absorbance data of the fluorescent active compound as a function of time. In other embodiments, other characteristics indicative of the concentrations of peracid and/or hydrogen peroxide in the sample may be measure, such as pH, oxidation-reduction potential, conductivity, mass spectra and/or combinations thereof. In such embodiments, the response data is the corresponding measured characteristic at the appropriate points in time.

Suitable exemplary detectors include photometric detectors, fluorometers, and/or optical cells/sensors/detectors. In an aspect a detector operates in the visible, ultraviolet or infrared wavelength range, although other luminescence detection techniques may also be used without departing from the scope of the present invention. Any suitable optical detector may be used without departing from the scope of the present invention, and that the invention is not limited in this respect.

In an aspect, a detector receives the sample mixture, and a processor collects the response data from detector. In the case of an optical detector, the response data is the measured change in the optical response of the detector over time. In some embodiments, detector measures response data by measuring the color change (e.g., absorbance or transmittance) of the sample solution within detector as a function of time. In other words, the voltage response of detector as a function of time corresponds to the amount of light transmitted through the sample mixture and hence the color the of the sample mixture as the chemical reaction progresses. The response data is indicative of the concentrations of peracid and hydrogen peroxide in the use composition.

In an aspect, suitable carriers or solvents for forming a use solution may include various types of water. In an aspect, deionized water, soft water and/or low grain (e.g. 5 grain) water is preferred for the use of certain detecting devices, namely for measuring conductivity. Beneficially, however, the type of water or solvent employed does not impact the optical measurements obtained from a composition according to the invention. However, it shall be understood that other suitable reagents and carriers may also be used without departing from the scope of the present invention, and that the invention is not limited in this respect.

The concentrations of peracid and/or hydrogen peroxide determined according to the methods of the invention may be used, for example, as feedback to a controller to maintain the peracid concentration in the use composition within a predefined range and/or to cause the emptying of a use composition vessel and production of a new use composition when the hydrogen peroxide concentration exceeds the maximum peroxide threshold concentration.

As an exemplary application of use, the methods for determining the concentrations of peracid and/or hydrogen peroxide according to the methods of the invention, may be used to ensure a use composition has a predefined range of such concentrations. For example, application specific concentrations may include: Aseptic bottle rinse generally requiring between about 1000-5000 ppm peracid and/or between about 5000-40,000 ppm hydrogen peroxide; or Central Sanitizing generally requiring between about 100-1000 ppm peracid and 100-5000 ppm hydrogen peroxide. If, for example, the concentration of peracid in the use composition decreases below a predetermined level, the use composition may be replenished by adding the concentrated equilibrium peracid composition according to the invention to the use composition.

As another example, if the concentration of hydrogen peroxide in the use composition exceeds a predetermined level, the use composition may be replenished by emptying the use composition vessel of the spent use composition and generating a new use composition using the concentrated equilibrium peracid composition according to the invention.

The various methods for detecting peracid and/or hydrogen peroxide concentration of a use solution according to the invention is based upon the correlation of the amount of the fluorescent active compound and the equilibrium peroxycarboxylic acid composition (e.g. the concentration of peroxycarboxylic acid that is required for the various cleaning and/or sanitizing applications of use of the invention). In an exemplary embodiment, the amount of fluorescent active compound added being proportional to the amount of the peroxycarboxylic acid. By using a fluorometer or other optical means to measure the fluorescent signal of the fluorescent active compound, the amount of the fluorescent active compound can be determined by using a calibration curve to relate the amount of fluorescent signal detected to the amount of the inert fluorescent active compound present. Because the inert fluorescent active compound and the peroxycarboxylic acid are formulated in known proportions, by knowing the amount of fluorescent active compound present then the amount of peroxycarboxylic acid present can be calculated.

The frequency at which the peracid and/or hydrogen peroxide concentration of a use solution is monitored according to the invention (e.g. monitoring frequency) will vary according to the desired applications of use. For example, a monitoring device may be programmed to monitor the concentrations of peracid and hydrogen peroxide in the use composition every 15 minutes, every 30 minutes, every hour, every two hours, every day or other appropriate time. The monitoring frequency/interval may vary depending on, among other things, the particular application to which the use composition is directed and the corresponding threshold concentrations of peracid and hydrogen peroxide. Beneficially, according to the invention, the fluorescent active compound is stable in the highly acidic, equilibrium peracid compositions according to the invention and allows measurement/detecting over such extended periods of time.

In an aspect, methods for determining the concentrations of one or more use compositions may apply to compositions undergoing kinetic reactions (e.g. obtaining response data from a peracid composition according to the invention over time). A use solution of the peracid composition of the present invention may be provided for measuring the concentration of peracid and/or hydrogen peroxide to obtain a desired measurement location (e.g. a location along a mixing profile). In such embodiments, the measurement location is to be selected to provide appropriate response data.

Methods of Use

In an aspect, the present invention includes use of the compositions for sanitizing surfaces and/or products. In another aspect, the compositions of the invention are particularly suitable for use as a hard surface sanitizer and/or disinfectant, a CIP sanitizer, food and/or tissue treatment sanitizer (including direct or indirect contact sanitizer), an environmental disinfectant, a laundry bleach and disinfectant, and/or an indirect food contact sanitizer. The present methods can be used in the methods, processes or procedures described and/or claimed in U.S. Pat. Nos. 5,200,189, 5,314,687, 5,718,910, 6,165,483, 6,238,685B1, 8,017,409 and 8,236,573, each of which are herein incorporated by reference in their entirety.

The methods of use are suitable for treating a variety of surfaces, products and/or target. For example, these may include a food item or a plant item and/or at least a portion of a medium, a container, an equipment, a system or a facility for growing, holding, processing, packaging, storing, transporting, preparing, cooking or serving the food item or the plant item. The present methods can be used for treating any suitable plant item. In some embodiments, the plant item is a grain, fruit, vegetable or flower plant item, a living plant item or a harvested plant item. In addition, the present methods can be used for treating any suitable food item, e.g., an animal product, an animal carcass or an egg, a fruit item, a vegetable item, or a grain item. In still other embodiments, the food item may include a fruit, grain and/or vegetable item.

The present methods can be used for treating a target that is at least a portion of a container, an equipment, a system or a facility for holding, processing, packaging, storing, transporting, preparing, cooking or serving the food item or the plant item. In some embodiments, the target is at least a portion of a container, an equipment, a system or a facility for holding, processing, packaging, storing, transporting, preparing, cooking or serving a meat item, a fruit item, a vegetable item, or a grain item. In other embodiments, the target is at least a portion of a container, an equipment, a system or a facility for holding, processing, packaging, storing, or transporting an animal carcass. In still other embodiments, the target is at least a portion of a container, an equipment, a system or a facility used in food processing, food service or health care industry. In yet other embodiments, the target is at least a portion of a fixed in-place process facility. An exemplary fixed in-place process facility can comprise a milk line dairy, a continuous brewing system, a pumpable food system or a beverage processing line.

The present methods can be used for treating a target that is at least a portion of a solid surface or liquid media. In some embodiments, the solid surface is an inanimate solid surface. The inanimate solid surface can be contaminated by a biological fluid, e.g., a biological fluid comprising blood, other hazardous body fluid, or a mixture thereof. In other embodiments, the solid surface can be a contaminated surface. An exemplary contaminated surface can comprise the surface of food service wares or equipment, or the surface of a fabric.

The various methods of treatment can include the use of any suitable level of the peroxycarboxylic acid. In some embodiments, the treated target composition comprises from about 10 ppm to about 1000 ppm of the peroxycarboxylic acid, including any of the peroxycarboxylic acid compositions according to the invention.

In still another aspect, the present invention includes water treatment methods and other industrial processes uses of the compositions for sanitizing surfaces and/or products. In some aspects, the invention includes methods of using the peroxycarboxylic acid compositions to prevent biological fouling in various industrial processes and industries, including oil and gas operations, to control microorganism growth, eliminate microbial contamination, limit or prevent biological fouling in liquid systems, process waters or on the surfaces of equipment that come in contact with such liquid systems. As referred to herein, microbial contamination can occur in various industrial liquid systems including, but not limited to, air-borne contamination, water make-up, process leaks and improperly cleaned equipment. In another aspect, the peroxycarboxylic acid compositions are used to control the growth of microorganisms in water used in various oil and gas operations. In a further aspect, the compositions are suitable for incorporating into fracturing fluids to control or eliminate microorganisms.

For the various industrial processes disclosed herein, "liquid system" refers to flood waters or an environment within at least one artificial artifact, containing a substantial amount of liquid that is capable of undergoing biological fouling, it includes but is not limited to industrial liquid systems, industrial water systems, liquid process streams, industrial liquid process streams, industrial process water systems, process water applications, process waters, utility waters, water used in manufacturing, water used in industrial services, aqueous liquid streams, liquid streams containing two or more liquid phases, and any combination thereof.

In at least one embodiment this technology would be applicable to any process or utility liquid system where microorganisms are known to grow and are an issue, and biocides are added. Examples of some industrial process water systems where the method of this invention could be applied are in process water applications (flume water, shower water, washers, thermal processing waters, brewing, fermentation, CIP (clean in place), hard surface sanitization, etc.), Ethanol/Bio-fuels process waters, pretreatment and utility waters (membrane systems, ion-exchange beds), water used in the process/manufacture of paper, ceiling tiles, fiber board, microelectronics, E-coat or electro deposition applications, process cleaning, oil exploration and energy services (completion and work over fluids, drilling additive fluids, fracturing fluids, flood waters, etc.; oil fields—oil and gas wells/flow line, water systems, gas systems, etc.), and in particular water systems where the installed process equipment exhibits lowered compatibility to halogenated biocides.

The methods by which the peroxycarboxylic acid compositions are introduced into the aqueous fluids or liquid systems are not critical. Introduction of the peracid compositions may be carried out in a continuous or intermittent manner and will depend on the type of water and/or liquid being treated. In some embodiments, the peracid compositions are introduced into an aqueous fluid according to the methods disclosed in U.S. patent application Ser. No. 13/645,671, titled "New Method and Arrangement for Feeding Chemicals into a Hydrofracturing Process and Oil and Gas Applications", which is hereby incorporated by reference in its entirety.

Those skilled in the art will recognize, or be able to ascertain using no more than routine experimentation, numerous equivalents to the specific procedures, embodiments, claims, and examples described herein. Such equivalents are considered to be within the scope of this invention and covered by the claims appended hereto. The contents of all references, patents, and patent applications cited throughout this application are hereby incorporated by reference to the same extent as if each individual publication or patent application was specifically and individually indicated as incorporated by reference. All publications and patent applications in this specification are indicative of the level of ordinary skill in the art to which this invention pertains. The invention is further illustrated by the following examples, which should not be construed as further limiting.

The various applications of use described herein provide the peroxycarboxylic acid compositions to a surface, liquid and/or product in need of antimicrobial and/or sanitizing treatment. Beneficially, the compositions of the invention are fast-acting. However, the present methods require a certain minimal contact time of the compositions with the surface, liquid and/or product in need of treatment for occurrence of sufficient antimicrobial effect. The contact time can vary with concentration of the use compositions, method of applying the use compositions, temperature of the use compositions, pH of the use compositions, amount of the surface, liquid and/or product to be treated, amount of soil or substrates on/in the surface, liquid and/or product to be treated, or the like. The contact or exposure time can be at least about 15 seconds. In some embodiments, the exposure time is about 1 to 5 minutes. In other embodiments, the exposure time is at least about 10 minutes, 30 minutes, or 60 minutes. In other embodiments, the exposure time is a few minutes to hours. In other embodiments, the exposure time is a few hours to days. The contact time will further vary based upon the concentration of peracid in a use solution.

The present methods can be conducted at any suitable temperature. In some embodiments, the present methods are conducted at a temperature ranging from about 0° C. to about 70° C., e.g., from about 0° C. to about 4° C. or 5° C., from about 5° C. to about 10° C., from about 11° C. to about 20° C., from about 21° C. to about 30° C., from about 31° C. to about 40° C., including at about 37° C., from about 41° C. to about 50° C., from about 51° C. to about 60° C., or from about 61° C. to about 70° C.

The compositions are suitable for antimicrobial efficacy against a broad spectrum of microorganisms, providing broad spectrum bactericidal and fungistatic activity. For example, the peracid biocides of this invention provide broad spectrum activity against wide range of different types of microorganisms (including both aerobic and anaerobic microorganisms), including bacteria, yeasts, molds, fungi, algae, and other problematic microorganisms.

The present methods can be used to achieve any suitable reduction of the microbial population in and/or on the target or the treated target composition. In some embodiments, the present methods can be used to reduce the microbial population in and/or on the target or the treated target composition by at least one $\log_{10}$. In other embodiments, the present methods can be used to reduce the microbial population in and/or on the target or the treated target composition by at least two $\log_{10}$. In still other embodiments, the present methods can be used to reduce the microbial population in and/or on the target or the treated target composition by at least three $\log_{10}$.

The peroxycarboxylic acid compositions may include concentrate compositions or may be diluted to form use compositions. In general, a concentrate refers to a composition that is intended to be diluted with water to provide a use solution that contacts a surface, liquid and/or product in need of treatment to provide the desired cleaning, sanitizing or the like. The peroxycarboxylic acid composition that contacts the surface, liquid and/or product in need of treatment can be referred to as a concentrate or a use composition (or use solution) dependent upon the formulation employed in methods according to the invention. It should be understood that the concentration of the peroxycarboxylic acid in the composition will vary depending on whether the composition is provided as a concentrate or as a use solution.

A use solution may be prepared from the concentrate by diluting the concentrate with water at a dilution ratio that provides a use solution having desired sanitizing and/or other antimicrobial properties. The water that is used to dilute the concentrate to form the use composition can be referred to as water of dilution or a diluent, and can vary from one location to another. The typical dilution factor is between approximately 1 and approximately 10,000 but will depend on factors including water hardness, the amount of soil to be removed and the like. In an embodiment, the concentrate is diluted at a ratio of between about 1:10 and about 1:10,000 concentrate to water. Particularly, the concentrate is diluted at a ratio of between about 1:100 and about 1:5,000 concentrate to water. More particularly, the concentrate is diluted at a ratio of between about 1:250 and about 1:2,000 concentrate to water.

All publications and patent applications in this specification are indicative of the level of ordinary skill in the art to which this invention pertains. All publications and patent applications are herein incorporated by reference to the same extent as if each individual publication or patent application was specifically and individually indicated as incorporated by reference.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

Example 1

The biocidal efficacy of various equilibrium peroxycarboxylic acid compositions shown in Table 2 according to the invention were evaluated under various conditions as set forth in Tables 3-5.

TABLE 2

| Material | Formula 1 wt-% | Formula 2 wt-% |
|---|---|---|
| Water | 20-40 | 20-40 |
| Sulfonated oleic acid (70%) | 1-20 | 1-20 |
| Octanoic acid | 1-25 | 1-25 |
| Acetic acid | 1-25 | 1-25 |
| Hydrogen Peroxide (35%) | 1-50 | 1-50 |
| Sulfuric acid (96%) | 5-20 | 5-20 |
| SCS (93%) | 0.5-7.5 | 0 |
| SXS (40%) | 0 | 0.5-7.5 |
| Additional Functional Ingredients (e.g. surfactant, stabilizing agent, defoaming agent) | 0-25 | 0-25 |

AOAC Official Method 960.09 (Germicidal and Detergent Sanitizing Action of Disinfectants) was employed to test the compositions for food contact sanitizing, as shown in Table 3.

TABLE 3

Food Contact Sanitizing Results

| Formula | Concentration | Exposure Time | pH | Test System | Log Reduction |
|---|---|---|---|---|---|
| 1 | 1 oz./6 gallons | 30 seconds | 5 | E. coli | 6.82 |
|  | 1 oz./7 gallons |  | 3 | S. aureus | 6.49 |
|  |  |  |  | E. coli | >6.99 |
|  |  |  | 5 | S. aureus | >7.13 |
|  |  |  |  | E. coli | 2.60 |

TABLE 3-continued

Food Contact Sanitizing Results

| Formula | Concentration | Exposure Time | pH | Test System | Log Reduction |
|---|---|---|---|---|---|
| 2 | 1 oz./6 gallons | 30 seconds | 5 | E. coli | 6.64 |
|  | 1 oz./7 gallons |  | 3 | S. aureus | 7.13 |
|  |  |  |  | E. coli | >6.99 |
|  |  |  | 5 | S. aureus | >7.13 |
|  |  |  |  | E. coli | 2.93 |

European Standard EN 1276 (November 2001) (Chemical Disinfectants and Antiseptics—Quantitative Suspension Test for the Evaluation of Bactericidal Activity of Chemical Disinfectants and Antiseptics Used in Food, Industrial, Domestic, and Institutional Areas) was employed to test the compositions against dirty soil conditions at 20° C., as shown in Table 4.

TABLE 4

EN 1276 Results

| Formula | Concentration | Exposure Time | pH | Test System | Log Reduction |
|---|---|---|---|---|---|
| 1 | 1 oz./6 gallons | 5 minutes | 2.5 | S. aureus | 4.20 |
|  |  |  |  | E. hirae | 3.70 |
|  |  |  |  | E. coli | >6.36 |
|  |  |  |  | P. aeruginosa | >6.26 |
| 2 | 1 oz./6 gallons | 5 minutes | 2.5 | S. aureus | 5.66 |
|  |  |  |  | E. hirae | 5.40 |
|  |  |  |  | E. coli | >6.34 |
|  |  |  |  | P. aeruginosa | >6.31 |

AOAC Official Method 964.02 (Testing Disinfectants—Use Dilution Methods) was employed to test the compositions at a more concentrated use solution, as shown in Table 5.

TABLE 5

UDT Results

| Formula | Concentration | Exposure Time | pH | Test System | # Negative Carriers/# Test Carriers |
|---|---|---|---|---|---|
| 1 | 1 oz./4 gallons | 10 minutes | 2.7 | S. aureus | 60/60 |
|  |  |  |  | P. aeruginosa | 60/60 |
| 2 | 1 oz./4 gallons | 10 minutes | 2.7 | S. aureus | 60/60 |
|  |  |  |  | P. aeruginosa | 58/60 |

Example 2

The formula stability of Formula 1 of Example 1 was evaluated under accelerated conditions, namely 100° F. over 4 weeks. The total peracid and hydrogen peroxide concentration was measured, as shown in FIG. 1. The results indicate that under the accelerated conditions, the highly acidic equilibrium peroxycarboxylic acid composition are stable for at least 4 weeks, which is equal to about a year under ambient conditions.

Example 3

A study was performed to determine the foam properties of selected compositions of the present invention, compared to peracid compositions including commercially available surfactants and/or defoaming agents. The following peracid compositions were prepared:

Test solution A: 2262 ppm composition A in soft water at pH 2.9 with sulfonated oleic acid and sodium octane sulfonate surfactants.

Test solution A (plus aluminum sulfate): 2262 ppm composition A in soft water at pH 2.9 with anionic surfactants, plus the aluminum sulfate defoaming agent.

Test solution B: 2262 ppm composition B in soft water at pH 2.9 with an anionic surfactant (commercially-available formulation).

Test solution C: 2262 ppm composition C in soft water at pH 2.9 (commercially-available formulation).

Test solution D: 2262 composition D in soft water pH 2.9 (commercially-available formulation).

A Glewwe Foam meter provides a dynamic foam test rather than a static test (as in the case of the Ross-Miles foam test). A dynamic foam meter is considered more appropriate for simulation of industrial conditions, e.g. the conditions in a flume. The equipment and general procedure for the Glewwe form test is described in U.S. Pat. No. 3,899,387, column 12, line 45 et seq, which is herein incorporated by reference in its entirety. The foam meter itself consists of a thermostated reservoir and a pump to recirculate the aqueous medium with foaming tendencies. The foam developed by the action of the aqueous stream impinging on the surface in the reservoir causes foam formation.

The foam heights of the tested compositions were determined using the following method. First 3000 mL of each formula was prepared and gently poured into Glewwe cylinder. The foam height is measured after various time intervals and provides a relative measure of the effectiveness of the defoamer. The reservoir of this foam meter consists of a stainless steel laboratory beaker of 3,000 mL capacity. Sealed to this beaker by means of a silicone sealant is a clear Plexiglass tubing which snugly fits into the inner walls of the beaker. This enables the operator to measure the foam height above the liquor level. The beaker measures about 19 cm high by about 17 to 18 cm in diameter and the Plexiglass tube extends about 30 to 35 cm above the lip of this beaker. Further detail regarding the Glewwe foam test is shown in, U.S. Pat. No. 5,447,648, which is expressly incorporated by reference herein.

A ruler was attached to the side of the cylinder, and the solution was level with the bottom of the ruler. The pump was turned on. Foam height was estimated by reading the average level of foaming according to the ruler. Foam height readings were taken versus time with a stopwatch or timer. The pump was turned off and height of the foam was recorded at various times. The results are shown in FIG. 2.

Figure 2:
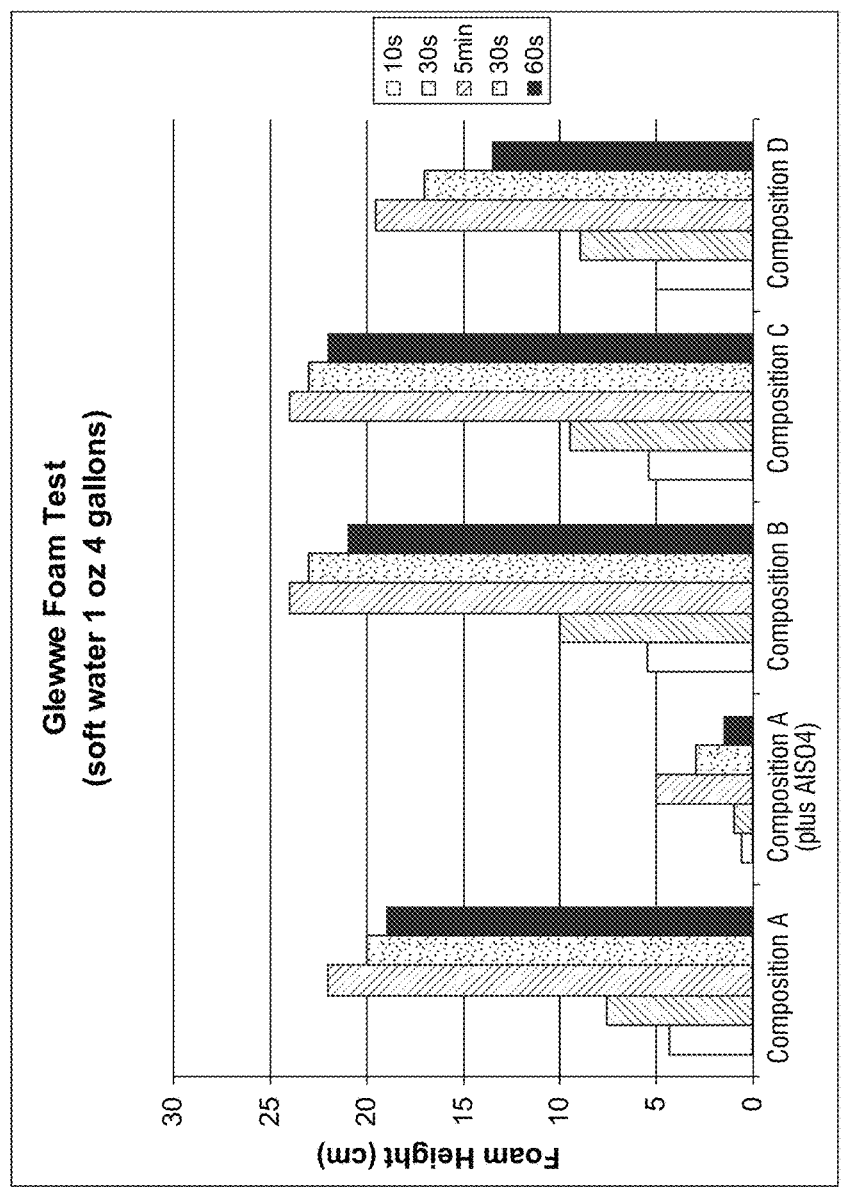
FIG. 2 shows a graph of the comparison of foam heights resulting from various commercially-available peroxycarboxylic acid compositions in comparison to the low-foaming, highly acidic peroxycarboxylic acid composition according to embodiments of the invention.

As shown in FIG. 2, the aluminum sulfate defoaming agent incorporated into the highly acidic peracid composition according to the invention, resulted in significant improvement in foam profile, as evidenced by the significantly lower foam height at all time points. The chart in FIG. 2 measured the impact of aluminum sulfate on the foam height of a peracid compositions in soft water, illustrating that the formulation containing the aluminum sulfate (test solution of Composition A plus aluminum sulfate) yielded significantly decreased foam height in comparison to several other commercial peracid compositions.

Beneficially, the reduced foam height of the compositions of the present invention is useful when using the compositions in applications where the production of foam is detrimental to the application, for example, in a clean in place cleaning and/or sanitizing application.

Example 4

A use solution of the concentrated equilibrium peroxycarboxylic acid composition according to the invention, as shown in Example 1 (equilibrium composition), was monitored by both conductivity and fluorescence.

Conductivity was measured by a conductivity meters; and the fluorescent intensity was measured by a hand hold fluorescent meter (made by Ecolab) with excitation wavelength at 275 nm. The emission of fluorescence was measured in SU and conductivity was measured in us/cm.

Figure 3:
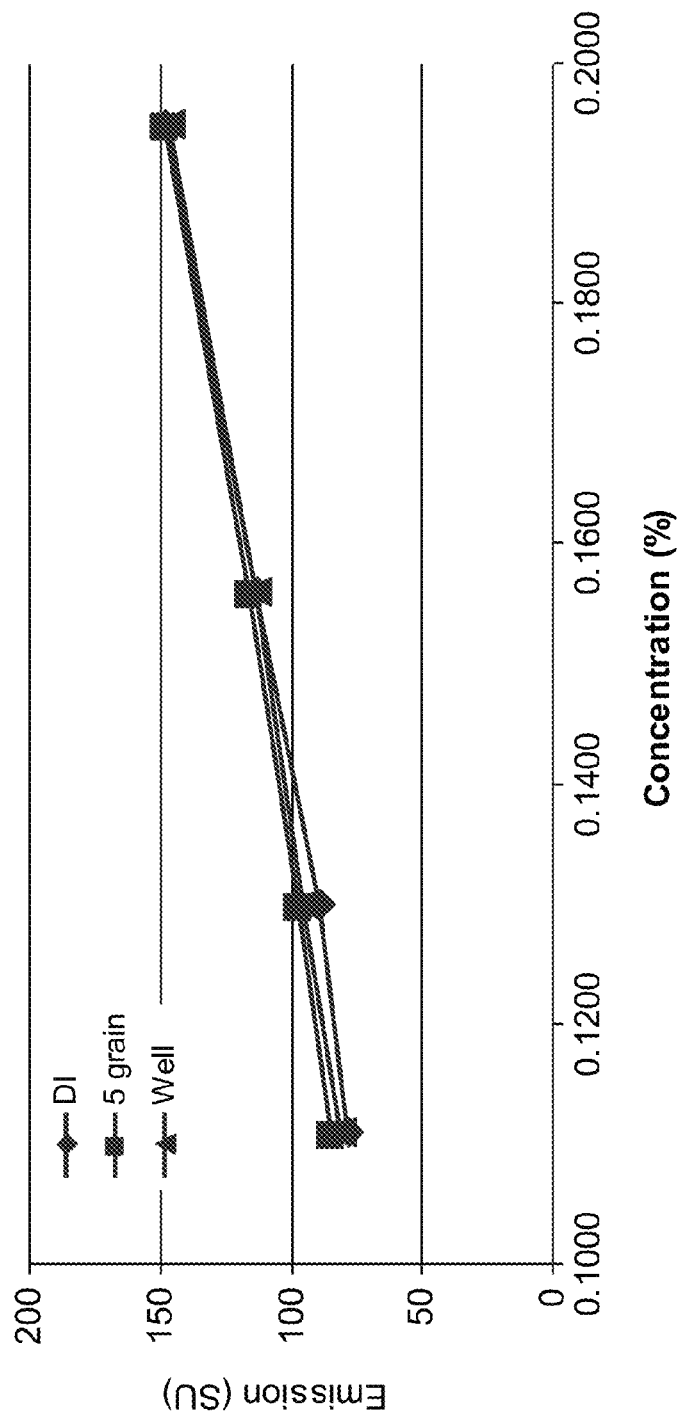
FIG. 3 shows a graph of the emission (SU) of the highly acidic peroxycarboxylic acid composition according to embodiments of the invention in various types of water.

As shown in FIG. 3, the increase of the concentration of peroxycarboxylic acid is proportional to the increase of the emission of the fluorescent active compound in all type of water tested, demonstrating the suitability of using the fluorescent active compounds to measure the concentration of peroxycarboxylic acid compositions according to the invention.

Figure 4:
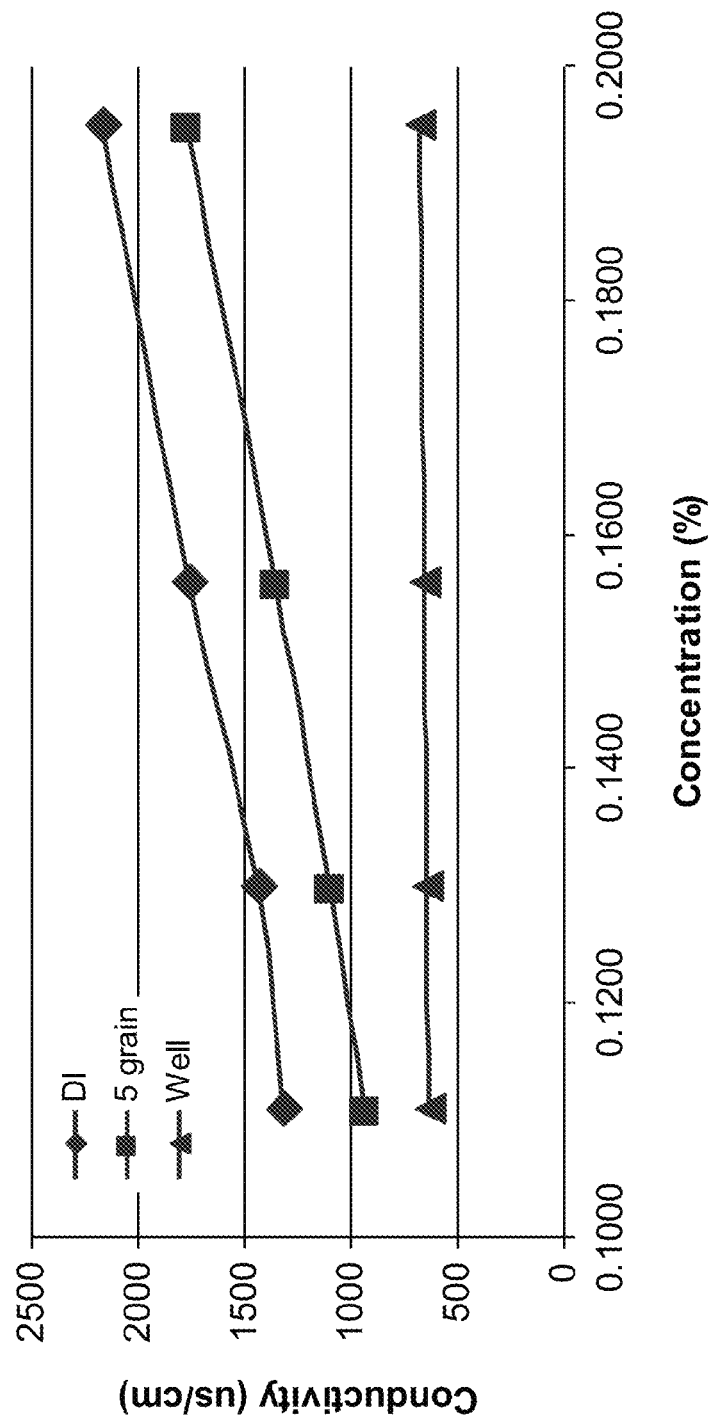
FIG. 4 shows a graph of the conductivity (us/cm) of the highly acidic peroxycarboxylic acid composition according to embodiments of the invention in various types of water.

As shown in FIG. 4, in deionized and 5 grain water, the emission intensity of the fluorescent active compound has linear relationship with the concentration of peroxycarboxylic acid, however such linear relationship does not hold in well water. This demonstrates the superiority of fluorescent according to this invention vs. conductivity approach in measuring the concentration of peroxycarboxylic acids.

The inventions being thus described, it will be obvious that the same may be varied in many ways. Such variations are not to be regarded as a departure from the spirit and scope of the inventions and all such modifications are intended to be included within the scope of the following claims. The above specification provides a description of the manufacture and use of the disclosed compositions and methods. Since many embodiments can be made without departing from the spirit and scope of the invention, the invention resides in the claims.

What is claimed is:

1. An equilibrium peracid composition comprising: a $C_1$-$C_{22}$ peroxycarboxylic acid;
   a $C_1$-$C_{22}$ carboxylic acid;
   hydrogen peroxide; and
   an aryl sulfonate fluorescent active compound, wherein the fluorescent active compound is stable in the equilibrium peracid composition for monitoring peroxycarboxylic acid concentration by an optical sensor, and provides a fluorescent emission equal to or greater than 0.01 SU in an aqueous solution and that is proportional to peroxycarboxylic acid concentration as measured by an optical sensor when the concentrated composition is diluted to from about 0.05 wt-% to about 0.25 wt-% in water,
   wherein the fluorescent active compound is sodium xylene sulfonate, toluene sulfonate, alkyl diphenyl oxide disulfonate, naphthalene sulfonate, alkyl naphthalene sulfonate, naphthalene disulfonate or sodium cumene sulfonate.

2. The composition of claim 1, wherein the $C_1$-$C_{22}$ peroxycarboxylic acid comprises from about 1 wt-% to about 40 wt-%, the $C_1$-$C_{22}$ carboxylic acid comprises from about 1 wt-% to about 80 wt-%, the hydrogen peroxide comprises from about 1 wt-% to about 80 wt-%, and the fluorescent active compound comprises from about 0.001 wt-% to about 10 wt-%.

3. The composition of claim 1, further comprising at least one additional agent selected from the group consisting of an acidulant, a hydrotrope, a solvent, a stabilizing agent, an anionic surfactant, an metal salt defoaming agent, and combinations thereof.

4. The composition of claim 1, wherein the $C_1$-$C_{22}$ peroxycarboxylic acid is a $C_2$-$C_{20}$ peroxycarboxylic acid and wherein the $C_1$-$C_{22}$ carboxylic acid is a $C_2$-$C_{20}$ carboxylic acid.

5. The composition of claim 4, wherein the peroxycarboxylic acid is peroxyacetic acid, peroxyoctanoic acid and/or peroxysulfonated oleic acid, and wherein the carboxylic acid is acetic acid, octanoic acid, sulfonated oleic acid or a combinations of the same.

6. The composition of claim 1, wherein the pH of the use solution is below about 4.

7. The composition of claim 1, further comprising an alkaline metal defoaming agent, an anionic surfactant, and a peroxycarboxylic acid stabilizing agent, wherein the stabilizing agent is a picolinic acid or a compound having the following Formula (IA):

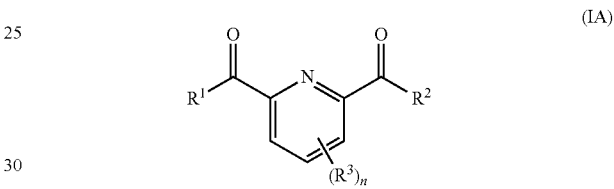

wherein $R^1$ is OH or —$NR^{1a}R^{1b}$, wherein $R^{1a}$ and $R^{1b}$ are independently hydrogen or $(C_1$-$C_6)$alkyl; wherein $R^2$ is OH or —$NR^{2a}R^{2b}$, wherein $R^{2a}$ and $R^{2b}$ are independently hydrogen or $(C_1$-$C_6)$alkyl; wherein each $R^3$ is independently $(C_1$-$C_6)$alkyl, $(C_2$-$C_6)$alkenyl or $(C_2$-$C_6)$alkynyl; and n is a number from zero to 3; or a salt thereof;

or a compound having the following Formula (IB):

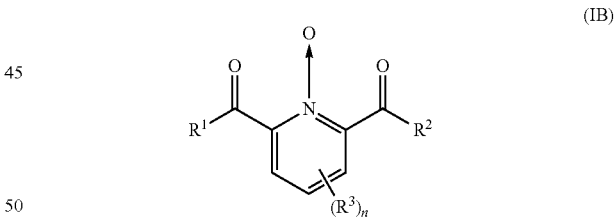

wherein $R^1$ is OH or —$NR^{1a}R^{1b}$, wherein $R^{1a}$ and $R^{1b}$ are independently hydrogen or $(C_1$-$C_6)$alkyl; wherein $R^2$ is OH or —$NR^{2a}R^{2b}$, wherein $R^{2a}$ and $R^{2b}$ are independently hydrogen or $(C_1$-$C_6)$alkyl; wherein each $R^3$ is independently $(C_1$-$C_6)$alkyl, $(C_2$-$C_6)$alkenyl or $(C_2$-$C_6)$alkynyl; and n is a number from zero to 3; or a salt thereof, wherein the stabilizing agent delays or prevents the peroxycarboxylic acid from exceeding its self-accelerating decomposition temperature (SADT).

* * * * *